United States Patent
Pei et al.

(10) Patent No.: US 6,552,076 B2
(45) Date of Patent: Apr. 22, 2003

(54) COMPOUNDS FOR ALTERING MITOCHONDRIAL FUNCTION AND CELLULAR RESPONSES

(75) Inventors: Yazhong Pei, San Diego, CA (US); Walter H. Moos, Oakland, CA (US); Soumitra S. Ghosh, San Diego, CA (US)

(73) Assignee: MitoKor, San Diego, CA (US)

( * ) Notice: Subject to any disclaimer, the term of this patent is extended or adjusted under 35 U.S.C. 154(b) by 0 days.

(21) Appl. No.: 10/020,090

(22) Filed: Dec. 14, 2001

(65) Prior Publication Data

US 2002/0173543 A1 Nov. 21, 2002

Related U.S. Application Data

(60) Provisional application No. 60/255,803, filed on Dec. 15, 2000.

(51) Int. Cl.$^7$ .............................................. A61K 31/24
(52) U.S. Cl. ..................... 514/533; 560/22; 562/405; 562/433; 562/444; 514/534
(58) Field of Search ................. 560/8, 19, 21, 560/22, 23, 43, 44, 48; 562/405, 433, 444; 514/579, 646, 649, 506, 532, 533, 534, 557, 568

(56) References Cited

U.S. PATENT DOCUMENTS

| | | | |
|---|---|---|---|
| 5,298,652 A | 3/1994 | Carson et al. | 562/444 |
| 5,936,065 A | * 8/1999 | Arrhenius et al. | 530/331 |
| 6,140,369 A | 10/2000 | Flitter et al. | 514/616 |

FOREIGN PATENT DOCUMENTS

WO     WO 99/55321     11/1999

OTHER PUBLICATIONS

CA:114:229348 abs of Indian Journal of Chemistry Section B: Organic Chemistry Including Med. Chem. by Nickel et al 30B (2) pp 182–187 1991.*
CA:128:162545 ab of Cancer Chemotherapy and Pharmacology 41 (2) pp 117–124 1998.*
Budd et al., "Mitochondrial and extramitochondrial apoptotic signaling pathways in cerebrocortical neurons," *P.N.A.S. USA* 97(11):6161–6166, May 23, 2000.
Corey and Tramontano, "Total Synthesis of Bongkrekic Acid," *J. Am. Chem. Soc.* 106:462–463, 1984.

* cited by examiner

Primary Examiner—Jean F. Vollano
(74) Attorney, Agent, or Firm—Seed IP Law Group, PLLC

(57) ABSTRACT

Compounds for treating diseases by altering mitochondrial function that affects cellular processes, as well as to compositions and methods related thereto. The compounds have the structure

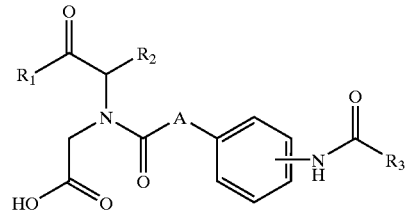

wherein $R_1$, $R_2$, $R_3$ and A are as defined herein.

18 Claims, No Drawings

COMPOUNDS FOR ALTERING MITOCHONDRIAL FUNCTION AND CELLULAR RESPONSES

BACKGROUND OF THE INVENTION

1. Field of the Invention

The present invention generally relates to compounds for treating diseases by altering mitochondrial function that affects cellular processes, as well as to compositions and methods related thereto.

2. Description of the Related Art

Mitochondria are the subcellular organelles that are the main energy source in cells of higher organisms, and provide direct and indirect biochemical regulation of a wide array of cellular respiratory, oxidative and metabolic processes. The electron transport chain (ETC) machinery resides in the mitochondrion, and drives oxidative phosphorylation to produce metabolic energy in the form of adenosine triphosphate (ATP). Mitochondria also play a critical role in maintaining intracellular calcium homeostasis. In addition to their role in energy production in growing cells, mitochondria (or, at least, mitochondrial components) are required for at least some forms of programmed cell death (PCD), also known as apoptosis (Newmeyer et al., *Cell* 79:353–364, 1994; Liu et al., *Cell* 86:147–157, 1996). Apoptosis is required for normal development of the nervous system and functioning of the immune system. However, some disease states are thought to be associated with either insufficient or excessive levels of apoptosis (e.g., cancer and autoimmune diseases in the first instance, and stroke damage and neurodegeneration in Alzheimer's disease in the latter case). For general reviews of apoptosis, and the role of mitochondria therein, see Green and Reed (*Science* 281:1309–1312, 1998), Green (*Cell* 94:695–698, 1998) and Kroemer (*Nature Medicine* 3:614–620, 1997).

Defective mitochondrial activity, including but not limited to failure at any step of the elaborate multi-complex mitochondrial assembly, known as the electron transport chain (ETC), may result in (i) decreases in ATP production, (ii) increases in the generation of highly reactive free radicals (e.g., superoxide, peroxynitrite and hydroxyl radicals, and hydrogen peroxide), (iii) disturbances in intracellular calcium homeostasis and (iv) the release of factors that initiate the apoptosis cascade. Because of these biochemical changes, mitochondrial dysfunction has the potential to cause widespread damage to cells and tissues. For example, oxygen free radical induced lipid peroxidation is a well established pathogenic mechanism in central nervous system (CNS) injury such as that found in a number of degenerative diseases, and in ischemia (i.e., stroke).

Cells from long-lived tissue that have high energy demands such as neurons, pancreatic islet cells, cardiac and muscle cells are particularly vulnerable to mitochondrial dysfunction. A number of degenerative diseases may thus be caused by or associated with either direct or indirect alterations in mitochondrial function. These include Alzheimer's Disease, diabetes mellitus, Parkinson's Disease, neuronal and cardiac ischemia, Huntington's disease and other related polyglutamine diseases (spinalbulbar muscular atrophy, Machado-Joseph disease (SCA-3), dentatorubro-pallidoluysian atrophy (DRPLA) and spinocerebellar ataxias, dystonia, Leber's hereditary optic neuropathy, schizophrenia, and myodegenerative disorders such as mitochondrial encephalopathy, lactic acidosis, and stroke (MELAS), and myoclonic epilepsy ragged red fiber syndrome (MERRF).

Increasing evidence points to the fundamental role of mitochondrial dysfunction in neurodegenerative diseases (Beal, *Biochim. Biophys. Acta* 1366: 211–223, 1998), and recent studies implicate mitochondria for regulating the events that lead to necrotic and apoptotic cell death (Susin et al., *Biochim. Biophys. Acta* 1366: 151–168, 1998). Stressed (stressors include free radicals, high intracellular calcium, loss of ATP, among others) mitochondria may release pre-formed soluble factors that can initiate apoptosis through an interaction with novel apoptosomes (Marchetti et al., *Cancer Res.* 56:2033–38, 1996; Li et al., *Cell* 91: 479–89, 1997). Release of preformed soluble factors by stressed mitochondria, like cytochrome c, may occur as a consequence of a number events. In some cases, release of apoptotic molecules (apoptogens) occurs when mitochondria undergo a sudden change in permeability to cytosolic solutes. This process has been termed "permeability transition". There is strong evidence that suggests that the loss of mitochondrial function may be due to the activation of the mitochondrial permeability transition pore, a $Ca^{2+}$ regulated inner membrane megachannel. Opening of the mitochondrial permeability transition pore results in the exchange of solutes that are less than 1500 daltons in size, collapse of the mitochondrial membrane potential, and uncoupling of the electron transport chain. In other cases, the permeability may be more subtle and perhaps more localized to restricted regions of a mitochondrion. In still other cases, overt permeability transition may not occur but apoptogens can still be released as a consequence of mitochondrial abnormalities. The magnitude of stress (ROS, intracellular calcium levels) influences the changes in mitochondrial physiology that ultimately determine whether cell death occurs via a necrotic or apoptotic pathway. To the extent that apoptotic cell death is a prominent feature of degenerative diseases, mitochondrial dysfunction may be a critical factor in disease progression.

Whereas mitochondria-mediated apoptosis may be critical in degenerative diseases, it is thought that disorders such as cancer involve the unregulated and undesirable growth (hyperproliferation) of cells that have somehow escaped a mechanism that normally triggers apoptosis in such undesirable cells. Enhanced expression of the anti-apoptotic protein, Bcl-2 and its homologues is involved in the pathogenesis of numerous human cancers. Bcl-2 acts by inhibiting programmed cell death and overexpression of Bcl-2 and the related Bcl-xL block mitochondrial release of cytochrome c from mitochondria and the activation of caspase 3 (Yang et al, *Science* 275:1129–1132, 1997; Kluck et al., *Science* 275:1132–1136, 1997; Kharbanda et al., *Proc. Natl. Acad. Sci. USA* 94:6939–6942, 1997). Bcl-2 also binds to several proteins that are involved in death regulation (Reed, *Nature* 387:773–779, 1997). Over expression of Bcl-2 and Bcl-xL protect against the mitochondrial dysfunction preceding nuclear apoptosis that is induced by chemotherapeutic agents. In addition, acquired multi-drug resistance to cytotoxic drugs is associated with inhibition cytochrome c release that is dependent on overexpression of Bcl-xL (Kojima et al., *J. Biol. Chem.* 273: 16647–16650, 1998). Because mitochondria have been implicated in apoptosis, it is expected that agents that interact with mitochondrial components will effect a cell's capacity to undergo apoptosis. Thus, agents that induce or promote apoptosis in hyperproliferative cells are expected to be useful in treating such hyperproliferative disorders and diseases.

Thus, alteration of mitochondrial function has great potential for a broad-based therapeutic strategy for designing drugs to treat degenerative diseases as well as hyperproliferative diseases. The mitochondrial permeability transition pore is a key target for the prevention of mitochondrial function collapse that leads to cell death, or the induction of apoptosis in cancer cells via dysregulation of mitochondria. This megachannel is a multi-protein complex in which the adenine nucleotide translocator (ANT) has been implicated as the critical molecular component.

ANT is located in the inner mitochondrial inner membrane and it facilitates transport of ADP and ATP across the mitochondrial inner membrane. In humans there are three genetic isoforms (ANT1, ANT2 and ANT3), each with different tissue expression patterns. ANT1 is highly expressed in heart and skeletal muscle and is induced during myoblast differentiation. ANT2 is overexpressed in a variety of hyperproliferative cells, tumors and neoplastically transformed cells with high glycolytic rates (Battini et al., *J. Biol. Chem.* 262:4355–4359, 1987; Torroni et al., *J. Biol. Chem.* 265:20589–20593, 1990; Faure-Vigny et al., *Mol. Carcinogen.* 16:165–172, 1996; Heddi et al., Biochim. *Biophys. Acta* 1316:203–209, 1996; and Giraud et al., *J. Mol. Biol.* 281:409–418, 1998). ANT3 is ubiquitously expressed in all tissues. ANT3 transcript level is proportional to the level of oxidative metabolism in a given tissue.

Two different conformations of ANT have been demonstrated on the basis of interactions with specific ligands, namely the inhibitors carboxyatractyloside (CATR) and bongkrekic acid (BKA). Ligands can bind to ANT in an asymmetric fashion, either from the matrix (m) or from the cytosolic (c) side of the inner mitochondrial membrane. For example, CATR binds to ANT in the c-conformation and induces permeability transition, while BKA interacts with ANT in the m-conformation and inhibits permeability transition in response to a variety of apoptotic stimuli (see, Budd et al., *PNAS US* 97:6161–6166, 2000) Different small molecule ligands of ANT isoforms therefore can possess a spectrum of activities—that is, they can act as cell protective agents targeted for degenerative diseases and as cytotoxic agents for hyperproliferative diseases.

Bongkrekic acid (BKA) is a polyenoic triacid that is produced by the microorganism *Pseudomonas cocovenenans*.

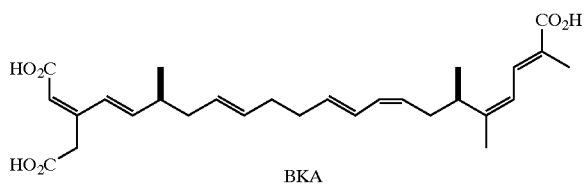

BKA

In the protonated form, BKA diffuses through the lipid phase of the inner mitochondrial membrane and binds to the matrix side of ANT with high affinity ($2\times10^{-8}$ M). Upon binding, BKA is believed to stabilize ANT in the m-conformation. Accordingly, BKA is believed to have significant potential as a cell-protective agent. Unfortunately, there are a number of problems associated with BKA. For example, large quantities of BKA are difficult to obtain by fermentation. While a convergent total synthesis of BKA has been reported (*J. Am. Chem. Soc.* 106:462–463, 1984), this technique involves 33 steps which makes it tedious to produce.

Accordingly, there is a need for agents that are cytotoxic with regard to undesirable cells and tissues, as well as agents that limit or prevent damage to desirable organelles, cells and tissues resulting from various consequences of mitochondrial dysfunction. In the former instance, such agents are desired to treat hyperproliferative diseases and disorders, or as species-specific antibiotics, herbicides or insecticides. In the latter instance, because mitochondria are essential organelles for producing metabolic energy, agents that protect mitochondria against injury are desired for the prevention, treatment and management of degenerative diseases, including mitochondria associated diseases. The present invention fulfills these needs and provides other related advantages.

BRIEF SUMMARY OF THE INVENTION

In brief, the present invention generally relates to compounds which inhibit mitochondrial permeability transition by binding to the adenine nucleotide translocator (ANT) in the m-conformation, and thereby have activity as cell-protective agents. In addition, this invention is directed to compositions containing a compound of this invention in combination with a pharmaceutically acceptable carrier or diluent, as well as to methods related to the administration of such compounds and/or composition to an animal in need thereof (including humans).

The compounds of this invention have the following general structure (I):

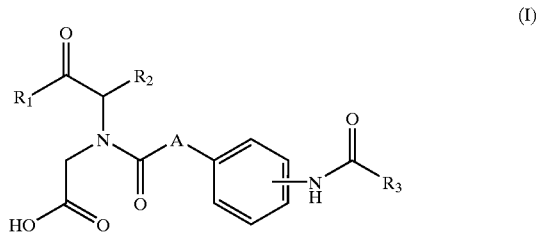

(I)

including stereoisomers, prodrugs and pharmaceutically acceptable salts thereof, wherein $R_1$, $R_2$, $R_3$ and A are as defined below.

The compounds of the invention are, in some aspects, mimics of bongkrekic acid (BKA) and function as agonists or antagonists of protein targets of BKA that elicit cell-protective or cytotoxic responses. In one embodiment, the target(s) of BKA that is (are) affected by a compound of the invention is (are) one or more isoforms of ANT. In a related embodiment, a compound of the invention binds preferentially to a specific isoform of ANT, but not to other ANT isoforms, from a single species of organism.

In embodiments wherein a compound of the invention is cytotoxic, the compound has, for example, remedial, therapeutic, palliative, rehabilitative, preventative, disease-impeditive or prophylactic activity with regard to hyperproliferative diseases and disorders such as cancer, psoriasis and the like. In such embodiments, a cytotoxic compound of the invention (a) binds preferentially to a specific isoform of ANT, but not to other ANT isoforms, from a single species of organism, wherein the preferentially-bound isoform of ANT is overexpressed in undesirable hyperproliferative cells; or (b) preferentially enters undesirable hyperproliferative cells.

In further embodiments wherein a compound of the invention is cytotoxic, the compound acts as a species-specific antibiotic, herbicide or insecticide. Such compounds binds preferentially to, respectively, (i) one or more ANT proteins from an undesirable parasitic or infective species (e.g., a eukaryotic parasite such as members of the Trypanosoma or Leishmania genera), but not to the corresponding ANT protein(s) from the host species (i.e., a mammal such as a human); (ii) one or more ANT proteins from an undesirable plant species (e.g., a weed), but not to the corresponding ANT protein(s) from desirable plants having economic value (e.g., crops or decorative plants), desirable insects (e.g., bees) or mammals including humans; or (iii) one or more ANT proteins from an undesirable insect (e.g., members of the genus Lepidoptera), but not to the corresponding ANT protein(s) from desirable insects, desirable plants or mammals including humans.

In embodiments wherein a compound of the invention is cyto-protective, the compound is used, for example, to prevent, treat or manage neurodegenerative diseases and disorders, (e.g., Alzheimer's disease and Parkinson's disease, or to ameliorate the undesirable effects of acute events such as ischemia or cardiac arrest.

These and other aspects of the present invention will become evident upon reference to the following detailed description and attached drawings. To that end, various references are set forth herein which describe in more detail certain aspects of this invention, and are each incorporated by reference in their entirety.

DETAILED DESCRIPTION OF THE INVENTION

As noted above, the present invention is generally directed to compounds and to pharmaceutical compositions containing the same, as well as to methods for treating diseases by altering mitochondrial function that affects cellular processes. The compounds of this invention have the following general structure (I):

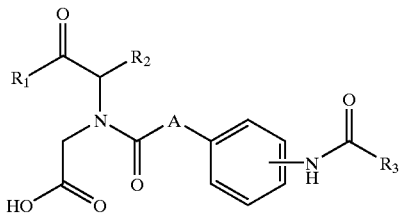

(I)

including stereoisomers, prodrugs and pharmaceutically acceptable salts thereof,
wherein:
A is a direct bond, alkyldiyl, substituted alkyldiyl, —O-(alkyldiyl)-, —O-(substituted alkyldiyl)-, -(alkyldiyl)-O—, -(substituted alkyldiyl)-O—, —N(R')-(alkyldiyl)-, —N(R')-(substituted alkyldiyl)-, -(alkyldiyl)-N(R')—, -(substituted alkyldiyl)-N(R')—, heterocyclediyl, substituted heterocyclediyl, heterocyclealkyldiyl or substituted heterocyclealkyldiyl, wherein R' is hydrogen or alkyl;

$R_1$ is hydroxy, alkoxy, aryloxy, arylalkyloxy, amino, or mono- or di-alkylamino;

$R_2$ is hydrogen, alkyl, substituted alky, aryl, substituted aryl, arylalkyl, substituted arylalkyl, heterocycle, substituted heterocycle, heterocylealkyl or substituted heterocyclealkyl; and $R_3$ is alkyl, substituted alky, aryl, substituted aryl, arylalkyl, substituted arylalkyl, heterocycle, substituted heterocycle, heterocylealkyl or substituted heterocyclealkyl.

As used herein, the terms used above have the following meaning:

"Alkyl" means a straight chain or branched, saturated or unsaturated, cyclic or non-cyclic hydrocarbon having from 1 to 10 carbon atoms, while "lower alkyl" has the same meaning but only has from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative saturated cyclic alkyls include cyclopropyl, cyclobutyl, cyclopentyl, cyclohexyl, (cycloalkyl)$CH_2$—, and the like; while unsaturated cyclic alkyls include cyclopentenyl and cyclohexenyl, and the like. Cycloalkyls are also referred to herein as "carbocyclic" rings systems, and include bi- and tri-cyclic ring systems having from 8 to 14 carbon atoms such as a cycloalkyl (such as cyclo pentane or cyclohexane) fused to one or more aromatic (such as phenyl) or non-aromatic (such as cyclohexane) carbocyclic rings.

"Alkyldiyl" means a divalent alkyl from which two hydrogen atoms are taken from the same carbon atom or from different carbon atoms, including divalent alkyl, alkenyl and alkynyl, as well as saturated and unsaturated carbocyclic rings as defined above.

"Halogen" means fluorine, chlorine, bromine or iodine.

"Oxo" means a carbonyl group (i.e., =O).

"Mono- or di-alkylamino" means an amino substituted with one alkyl or with two alkyls, respectively.

"Alkoxy" means —O-(alkyl).

"Aryloxy" means —O-(aryl).

"Arylalkyloxy" means —O-(arylalkyl).

"Aryl" means an aromatic carbocyclic moiety such as phenyl or naphthyl.

"Arylalkyl" means an alkyl having at least one alkyl hydrogen atom replaced with an aryl moiety, such as benzyl, —$(CH_2)_2$phenyl, —$(CH_2)_3$phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like. "Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclediyl" means a divalent heterocycle from which two hydrogen atoms are taken from the same atom or from different atoms.

"Heterocyclealkyl" means an alkyl having at least one alkyl hydrogen atom replaced with a heterocycle, such as —CH₂morpholinyl, and the like.

"Heterocylcealkyldiyl" means a divalent heterocyclealkyl from which two hydrogen atoms are taken from the same atom or from different atoms.

The term "substituted" as used herein means any of the above groups (i.e., alkyl, aryl, arylalkyl, heterocycle, heterocyclealkyl, alkyldiyl, heterocyclediyl and heterocylcealkyldiyl) wherein at least one hydrogen atom is replaced with a substituent. In the case of an oxo substituent ("=O") two hydrogen atoms are replaced. Substituents include halogen, hydroxy, oxoalkyl, substituted alkyl (such as haloalkyl, mono- or di-substituted aminoalkyl, alkyloxyalkyl, and the like), aryl, substituted aryl, arylalkyl, substituted arylalkyl, heterocycle, substituted heterocycle, heterocyclealkyl, substituted heterocyclealkyl, —NR$_a$R$_b$, —NR$_a$C(=O)R$_b$, —NR$_c$C(=O)NR$_a$R$_b$, —NR$_a$C(=O)OR$_b$—NR$_a$SO$_2$R$_b$, —OR$_a$, —C(=O)R$_a$—C(=O)OR$_a$—C(=O)NR$_a$R$_b$, —OC(=O)R$_a$, —OC(=O)OR$_a$, —OC(=O)NR$_a$R$_b$, —NR$_a$SO$_2$R$_b$, or a radical of the formula —Y—Z—R$_a$ where Y is alkanediyl, substituted alkanediyl, or a direct bond, Z is —O—, —S—, —S(=O)—, —S(=O)$_2$—, —N(R$_b$)—, —C(=O)—, —C(=O)O—, —OC(=O)—, —N(R$_b$)C(=O)—, —C(=O)N(R$_b$)—or a direct bond, wherein R$_a$, R$_b$ and R$_c$ are the same or different and independently hydrogen, amino, alkyl, substituted alkyl (including halogenated alkyl), aryl, substituted aryl, arylalkyl, substituted arylalkyl, heterocycle, substituted heterocycle, heterocylealkyl or substituted heterocyclealkyl, or wherein R$_a$ and R$_b$ taken together with the nitrogen atom to which they are attached form a heterocycle or substituted heterocycle.

In one embodiment, A is a direct bond and the compounds have the following structure (II):

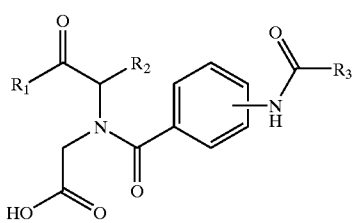

(II)

In another embodiments, and depending upon the choice of A, the compounds have one of the following structures (III) through (IX), wherein each of alkyldiyl, heterocyclediyl and/or heterocylcealkyldiyl moieties may be unsubstituted or substituted with one or more substituents as defined above.

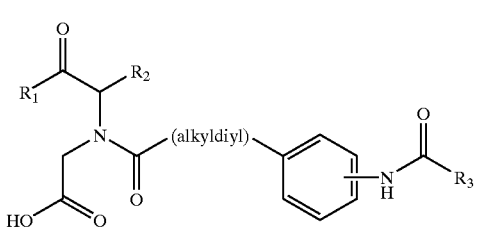

(III)

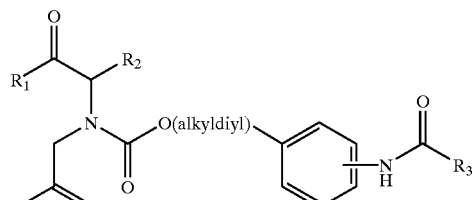

(IV)

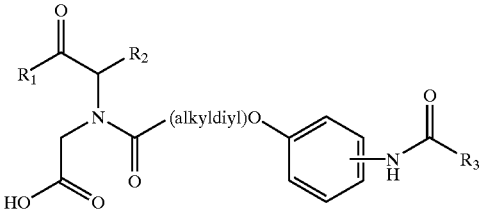

(V)

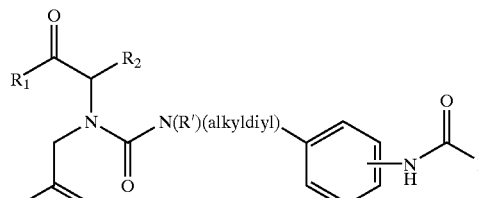

(VI)

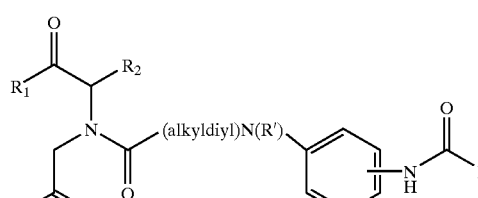

(VII)

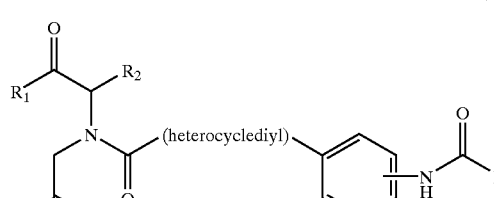

(VIII)

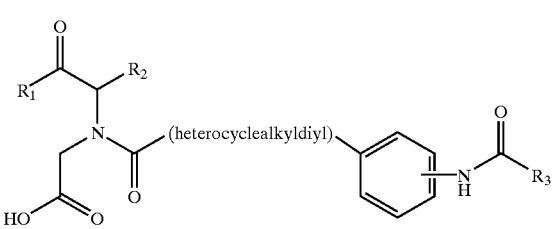

(IX)

The compounds of the present invention may generally be utilized as the free acid or base. Alternatively, the compounds of this invention may be used in the form of acid or based addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Based addition salts include the ammonium ion, other suitable cations. Thus, the term "pharmaceutically acceptable salt" of structure (I) is intended to encompass any and all acceptable salt forms. Suitable salts in this context may be found in *Remington's Pharmaceuitcal Sciences,* 17$^{th}$ ed., Mack Publishing Co., Easton, Pa., 1985, which is hereby incorporated by reference.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The compounds of this invention are typically formulated in conjunction with a suitable pharmaceutical carrier or diluent, and such compositions may be in any form that allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, which is the route of administration in preferred embodiments, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more agents that impair MCA activity, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of an agent that impairs MCA activity as provided herein such that a suitable dosage will be obtained. Typically, this amount is at least 0.01 wt % of the agent in the composition. When intended for oral administration, this amount may be varied to be between 0.1 and about 70% of the weight of the composition. Preferred oral compositions contain between about 4% and about 50% of the agent(s) that alter mitochondrial function. Preferred compositions and preparations are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the agent that impairs MCA activity of from about 0.1 to about 10% w/v (weight per unit volume).

The composition may be intended for rectal administration, in the form, e.g., of a suppository that will melt in the rectum and release the drug. The composition for rectal administration may contain an oleaginous base as a suitable nonirritating excipient. Such bases include, without limitation, lanolin, cocoa butter and polyethylene glycol. In the methods of the invention, the agent(s) that alter mitochondrial function identified as described herein may be administered through use of insert(s), bead(s), timed-release formulation(s), patch(es) or fast-release formulation(s).

It will be evident to those of ordinary skill in the art that the optimal dosage of the compound may depend on the weight and physical condition of the patient; on the severity and longevity of the physical condition being treated; on the particular form of the active ingredient, the manner of administration and the composition employed. The use of the minimum dosage that is sufficient to provide effective therapy is usually preferred. Patients may generally be monitored for therapeutic or prophylactic effectiveness using assays suitable for the condition being treated or prevented, which will be familiar to those having ordinary skill in the art and which, as noted above, will typically involve determination of whether circulating insulin and/or glucose concentrations fall within acceptable parameters according to well-known techniques. Suitable dose sizes will vary with the size, condition and metabolism of the patient, but will typically range from about 10 mL to about 500 mL for 10–60 kg individual. It is to be understood that according to certain embodiments the agent may be membrane permeable, preferably permeable through the plasma membrane and/or through mitochondrial outer and/or inner membranes. According to certain other embodiments, the use of a compound as disclosed herein in a chemotherapeutic composition can involve such an agent being bound to another compound, for example, a monoclonal or polyclonal antibody, a protein or a liposome, which assist the delivery of said agent.

Another embodiment of the invention involves the creation and identification of compounds that increase the degree or enhance the rate of apoptosis in hyperproliferative cells present in diseases and disorders such as cancer and psoriasis (note that, for the purposes of the disclosure, the term "hyperproliferative disease or disorder" specifically excludes pregnancy). Because oncogenic changes render certain tumors more susceptible to apoptosis (Evan and Littlewood, *Science* 281:1317,1998), such agents are expected to be useful for treating such hyperproliferative diseases or disorders. In a related embodiment, a biological sample from a patient having or suspected of having a hyperproliferative disease or disorder are evaluated for their susceptibility to such agents using the methods of the invention. Cybrid cells are a preferred biological sample in this embodiment.

A further embodiment of the invention involves the creation and identification of agents that alter mitochondrial function and/or selectively affect MPT in mitochondria and/or cell death in a species-specific manner. By "species-specific manner" it is meant that such agents affect MPT or cell death in a first organism belonging to one species but not in a second organism belonging to another species. This embodiment of the invention is used in a variety of methods.

For example, this embodiment of the invention to identify agents that selectively induce MPT and/or apoptosis in biological samples comprising cells or mitochondria derived from different species, e.g., in trypanasomes (Ashkenazi and Dixit, *Science* 281:1305, 1998), and other eukaryotic pathogens and parasites, including but not limited to insects, but which do not induce MPT and/or apoptosis in their mammalian hosts. Such agents are expected to be useful for the prophylactic or therapeutic management of such pathogens and parasites.

As another example, this embodiment of the invention is used to create and identify agents that selectively induce MPT and/or apoptosis in biological samples comprising cells or mitochondria derived from undesirable plants (e.g., weeds) but not in desirable plants (e.g., crops), or in undesirable insects (in particular, members of the family Lepidoptera and other crop-damaging insects) but not in desirable insects (e.g., bees) or desirable plants. Such agents are expected to be useful for the management and control of such undesirable plants and insects. Cultured insect cells, including for example, the Sf9 and Sf21 cell lines derived from *Spodoptera frugiperda*, and the HIGH FIVE (cell line from *Trichopolusia ni* (these three cell lines are available from InVitrogen, Carlsbad, Calif.) may be biological sample in certain such embodiments of the invention.

The suitability of a compound for treatment of a subject having a disease associated with altered mitochondrial function may be determined by various assay methods. Such compounds are active in one or more of the following assays for measuring mitochondrial permeability transition, or in any other assay known in the art that directly or indirectly measures induction of MPT, MPT itself or any downstream sequelae of MPT, or that may be useful for identifying mitochondrial permeability pore components (i.e., molecules that regulate MPT). Accordingly, it is also an aspect of the invention to provide compositions and methods for treating a disease associated with altered mitochondrial function by administering a composition that regulates MPT. In embodiments of the invention, agents to be formulated into such compositions may be identified by the following assay methods.

A. Assay for Mitochondrial Permeability Transition (MPT) Using 2-,4-Dimethylaminostyryl-N-Methylpyridinium (DASPMI)

According to this assay, one may determine the ability of a compound of the invention to inhibit the loss of mitochondrial membrane potential that accompanies mitochondrial dysfunction. As noted above, maintenance of a mitochondrial membrane potential ($\Delta\Psi m$) may be compromised as a consequence of mitochondrial dysfunction. This loss of membrane potential, or mitochondrial permeability transition (MPT), can be quantitatively measured using the mitochondria-selective fluorescent probe 2-,4-dimethylaminostyryl-N-methylpyridinium (DASPMI).

Upon introduction into cell cultures, DASPMI accumulates in mitochondria in a manner that is dependent on, and proportional to, mitochondrial membrane potential. If mitochondrial function is disrupted in such a manner as to compromise membrane potential, the fluorescent indicator compound leaks out of the membrane bounded organelle with a concomitant loss of detectable fluorescence. Fluorimetric measurement of the rate of decay of mitochondria associated DASPMI fluorescence provides a quantitative measure of loss of membrane potential, or MPT. Because mitochondrial dysfunction may be the result of multiple factors that directly or indirectly induce MPT as described above (e.g., ROS, calcium flux), agents that retard the rate of loss of DASPMI fluorescence may be effective agents for treating diseases associated with altered mitochondrial function, according to the methods of this invention.

B. Assay of Apoptosis in Cells Treated with Mitochondria Protecting Agents

As noted above, mitochondrial dysfunction may be an induction signal for cellular apoptosis. According to this assay, one may determine the ability of a compound agent to inhibit or delay the onset of apoptosis. Mitochondrial dysfunction may be present in cells known or suspected of being derived from a subject having a disease associated with altered mitochondrial function, or mitochondrial dysfunction may be induced in normal cells by one or more of a variety of physiological and biochemical stimuli, with which those having skill in the art will be familiar.

In one aspect of the apoptosis assay, cells that are suspected of undergoing apoptosis may be examined for morphological, permeability or other changes that are indicative of an apoptotic state. For example, apoptosis in many cell types may cause altered morphological appearance such as plasma membrane blebbing, cell shape change, loss of substrate adhesion properties or other morphological changes that can be readily detected by those skilled in the art using light microscopy. As another example, cells undergoing apoptosis may exhibit fragmentation and disintegration of chromosomes, which may be apparent by microscopy and/or through the use of DNA specific or chromatin specific dyes that are known in the art, including fluorescent dyes. Such cells may also exhibit altered plasma membrane permeability properties as may be readily detected through the use of vital dyes (e.g., propidium iodide, trypan blue) or by the detection of lactate dehydrogenase leakage into the extracellular milieu. These and other means for detecting apoptotic cells by morphologic criteria, altered plasma membrane permeability and related changes will be apparent to those familiar with the art.

In another aspect of an apoptosis assay, translocation of cell membrane phosphatidylserine (PS) from the inner to the outer leaflet of the plasma membrane is detected by measuring outer leaflet binding by the PS-specific protein annexin (Martin et al., *J. Exp. Med.* 182:1545, 1995; Fadok et al., *J. Immunol.* 148:2207, 1992.) In another aspect of the apoptosis assay, induction of specific protease activity in a family of apoptosis-activated proteases known as the caspases is measured, for example, by determination of caspase-mediated cleavage of specifically recognized protein substrates. These substrates may include, for example, poly-(ADP-ribose) polymerase (PARP) or other naturally occurring or synthetic peptides and proteins cleaved by caspases that are known in the art (see, e.g., Ellerby et al., *J. Neurosci.* 17:6165, 1997). The synthetic peptide Z-Tyr-Val-Ala-Asp-AFC, wherein "Z" indicates a benzoyl carbonyl moiety and AFC indicates 7-amino-4-trifluoromethylcoumarin (Kluck et al., *Science* 275:1132, 1997; Nicholson et al., *Nature* 376:37, 1995), is one such substrate. Other substrates include nuclear proteins such as U1–70 kDa and DNA-PKcs (Rosen and Casciola-Rosen, *J. Cell. Biochem.* 64:50, 1997; Cohen, *Biochem. J.* 326:1, 1997).

As described above, the mitochondrial inner membrane may exhibit highly selective and regulated permeability for many small molecules, including certain cations, but is impermeable to large (>~10 kDa) molecules (see, e.g., Quinn, 1976 The Molecular Biology of Cell Membranes, University Park Press, Baltimore, Md.). Thus, in another aspect of the apoptosis assay, detection of the mitochondrial protein cytochrome c that has leaked out of mitochondria in apoptotic cells may provide an apoptosis indicator that can be readily determined (Liu et al., *Cell* 86:147, 1996). Such detection of cytochrome c may be performed spectrophotometrically, immunochemically or by other well established methods for determining the presence of a specific protein.

Release of cytochrome c from cells challenged with apoptotic stimuli (e.g., ionomycin, a well-known calcium ionophore) can be followed by a variety of immunological methods. Matrix-assisted laser desorption ionization time-of-flight (MALDI-TOF) mass spectrometry coupled with affinity capture is particularly suitable for such analysis since apo-cytochrome c and holo-cytochrome c can be distinguished on the basis of their unique molecular weights. For example, the Surface-Enhanced Laser Desorption/Ionization (SELDITM) system (Ciphergen, Palo Alto, Calif.) may be utilized to follow the inhibition by mitochondria protecting agents of cytochrome c release from mitochondria in ionomycin treated cells. In this approach, a cytochrome c specific antibody immobilized on a solid support is used to capture released cytochrome c present in a soluble cell extract. The captured protein is then encased in a matrix of an energy absorption molecule (EAM) and is desorbed from the solid support surface using pulsed laser excitation. The molecular mass of the protein is determined by its time of flight to the detector of the SELDITM mass spectrometer.

The person of ordinary skill in the art will readily appreciate that there may be other suitable techniques for quantifying apoptosis, and such techniques for purposes of determining the effects of mitochondria protecting agents on the induction and kinetics of apoptosis are within the scope of the assays disclosed here.

C. Assay of Electron Transport Chain (ETC) Activity in Isolated Mitochondria

As described above, mitochondria associated diseases may be characterized by impaired mitochondrial respiratory activity that may be the direct or indirect consequence of elevated levels of reactive free radicals such as ROS, of elevated cytosolic free calcium concentrations or other stimuli. Accordingly, a compound for use in the treatment of a disease associated with altered mitochondrial function may restore or prevent further deterioration of ETC activity in mitochondria of individuals having mitochondria associated diseases. Assay methods for monitoring the enzymatic activities of mitochondrial ETC Complexes I, II, III, IV and ATP synthetase, and for monitoring oxygen consumption by mitochondria, are well known in the art (see, e.g., Parker et al., *Neurology* 44:1090–96, 1994; Miller et al., *J. Neurochem.* 67:1897, 1996). It is within the scope of the methods provided by this invention to identify a suitable compound using such assays of mitochondrial function, given the relationship between mitochondrial membrane potential and ETC activity as described above. Further, mitochondrial function may be monitored by measuring the oxidation state of mitochondrial cytochrome c at 540 nm. Also as described above, oxidative damage that may arise in mitochondria associated diseases may include damage to mitochondrial components such that the oxidation state of cytochrome c, by itself or in concert with other parameters of mitochondrial function including, but not limited to, mitochondrial oxygen consumption, may be an indicator of reactive free radical damage to mitochondrial components. Accordingly, the invention provides various assays designed to test the inhibition of such oxidative damage by compounds that may influence mitochondrial membrane permeability. The various forms such assays may take will be appreciated by those familiar with the art, and are not intended to be limited by the disclosures herein, including in the Examples.

For example, Complex IV activity may be determined using commercially available cytochrome c that is fully reduced via exposure to excess ascorbate. Cytochrome c oxidation may then be monitored spectrophotometrically at 540 nm using a stirred cuvette in which the ambient oxygen above the buffer is replaced with argon. Oxygen reduction in the cuvette may be concurrently monitored using a micro oxygen electrode with which those skilled in the art will be familiar, where such an electrode may be inserted into the cuvette in a manner that preserves the argon atmosphere of the sample, for example through a sealed rubber stopper. The reaction may be initiated by addition of a cell homogenate or, preferably a preparation of isolated mitochondria, via injection through the rubber stopper. In the assay described here, for example, a defect in complex IV activity may be correlated with an enzyme recognition site. This assay, or others based on similar principles, may permit correlation of mitochondrial respiratory activity with mitochondria membrane permeability, which may be determined according to other assays described herein.

The following examples are offered by way of illustration, and not by way of limitation.

EXAMPLES

Example 1

SYNTHESIS OF REPRESENTATIVE COMPOUNDS OF STRUCTURE (I)

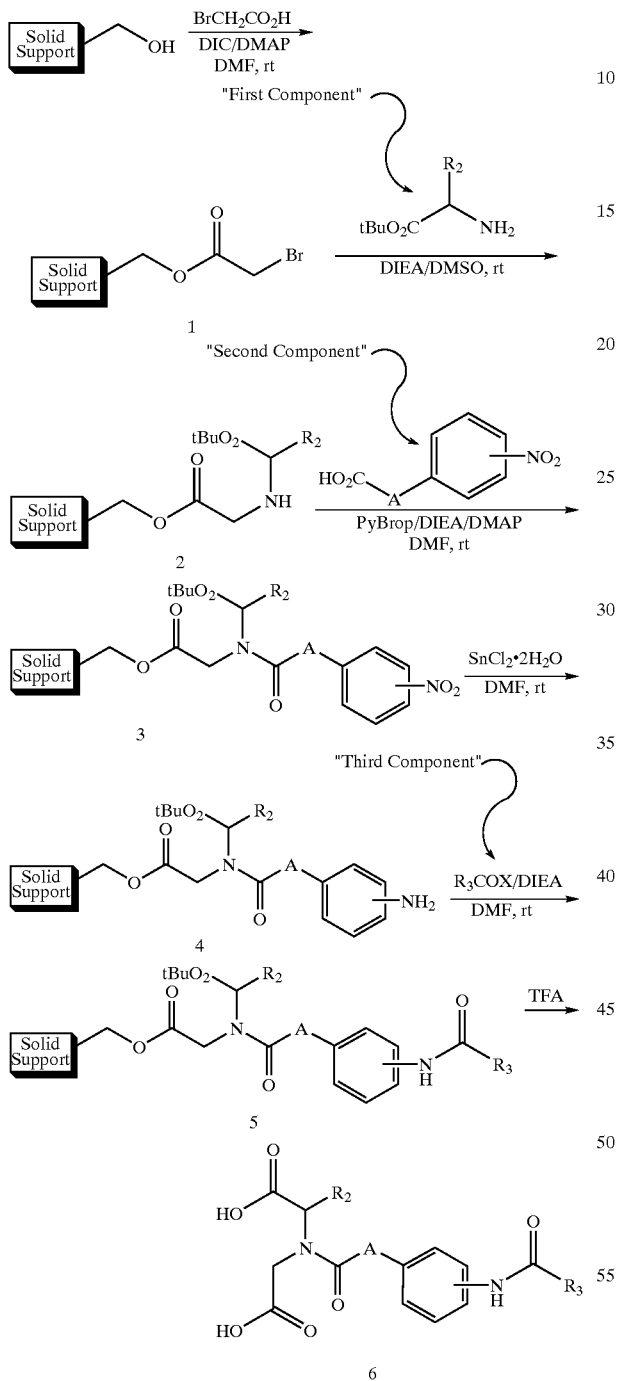

STEP 1: Coupling Bromoacetic Acid on to Wang Resin

Polystyrene Wang resin (10.0 g, 1.25 mmol/g) was shaken at room temperature with bromoacetic acid (8.68 g, 62.5 mmol), diisopropylcarbodiimide (DIC) (9.79 ml, 62.5 mmol) and 4-dimethylaminopyridine (DMAP) (100 mg) in DMF (60 ml) in a polypropylene bottle for 4 hours. The resin was collected via vacuum filtration using a 50 ml polypropylene syringe fitted with a polyethylene frit, and washed with DMF (3×40 ml), methanol (3×40 ml), DMF (3×40 ml), methanol (3×40 ml), DCM (3×40 ml), methanol (3×40 ml), and air dried. The resulted bromoacetate resin 1 (12.0 g) was used in the next step without further analysis.

STEP 2: Displacement Reaction with Amino Esters a. Bromoacetate resin 1 (4.0 g) was shaken with glycine t-butyl ester HOAc salt (3.82 g, 20.0 mmol) and diisopropylethylamine (DIEA) (7.2 ml, 75 mmol) in DMSO (13 ml) in a 20 ml polypropylene syringe fitted with a polyethylene frit at room temperature for 24 hours. The resin was washed with DMF (3×20 ml), methanol (3×20 ml), DMF (3×20 ml), methanol (3×20 ml), DCM (3×20 ml), methanol (3×20 ml), and air dried. The resulted resin 2A was used in the next step without further analysis.

b. Bromoacetate resin 1 (4.0 g) was treated with aspartic acid di-t-butyl ester HCl salt in the same manner as described in 2a. The resulted resin 2B was used in the next step without further analysis.

c. Bromoacetate resin 1 (4.0 g) was treated with glutaric acid di-t-butyl ester HCl salt in the same manner as described in 2a. The resulted resin 2C was used in the next step without further analysis.

STEP 3: Coupling Reaction with Nitrobenzoic Acids (A=Direct Bond)

a. One-third of resin 2A was shaken with 2-nitrobenzoic acid (1.16 g, 6.9 mmol), DIEA (2.0 ml, 11.5 mmol), and bromo-(tris-pyrrolidino)phosphonium hexafluorophasphate(PyBrop) (3.26 g, 7.0 mmol) in DMF (10 ml) at room temperature overnight. The resin was washed with DMF (3×10 ml). The reaction was repeated to ensure complete coupling. The resin was washed with DMF (3×10 ml), methanol (3×10 ml), DMF (3×10 ml), methanol (3×10 ml), DCM (3×10 ml), mathanol (3×10 ml), and air dried. A small sample (~50 mg) of the resulted resin 3AA was treated with TFA/water (95/5, 1.0 ml) for 1 hour at room temperature. The solution was collected via filtration. The resin was washed with acetic acid (3×1 ml). The combined solution was lyophilized. The residue was analyzed by 1H NMR and mass spectrometry. $^1$H NMR (CD$_3$OD)__ 8.25(m, 1H), 7.82(m, 1H), 7.72(m, 1H), 7.54(m, 1H), 4.38(s, 2H), 4.07(s, 2H). MS calcd. for $C_{11}H_{10}N_2O_7$: 282.05, found: 281(M-H).

b. One-third of resin 2A was reacted with 3-nitrobenzoic acid in the same manner as described in 3a to yield resin 3AB. $^1$H NMR (CD$_3$OD) __8.37(m, 1H), 8.32(m, 1H), 7.84(m, 1H), 7.74(m, 1H), 4.31(s, 2H), 4.12(s, 2H). MS calcd. for $C_{11}H_{10}N_2O_7$: 282.05, found: 281 (M-H).

c. One third of resin 2A was reacted with 4-nitrobenzoic acid in the same manner as described in 3a to yield resin 3AC. $^1$H NMR (CD$_3$OD) __8.33(d, 2H), 7.67(d, 2H), 4.31(s, 2H), 4.09(s, 2H). MS calcd. for $C_{11}H_{10}N_2O_7$: 282.05, found: 281(M-H).

d. One-third of resin 2B was reacted with 2-nitrobenzoic acid in the same manner as described in 3a to yield resin 3BA. MS calcd. for $C_{13}H_{12}N_2O_9$: 340.05, found: 339(M-H).

e. One-third of resin 2B was reacted with 3-nitrobenzoic acid in the same manner as described in 3a to yield resin 3BB. MS calcd. for $C_{13}H_{12}N_2O_9$: 340.05, found: 339(M-H).

f. One-third of resin 2B was reacted with 4-nitrobenzoic acid in the same manner as described in 3a to yield resin 3BC. MS calcd. for $C_{13}H_{12}N_2O_9$: 340.05, found: 339(M-H).

g. One-third for resin 2C was reacted with 2-nitrobenzoic acid in the same manner as described in 3a to yield resin 3CA. MS calcd. for $C_{14}H_{14}N_2O_9$: 354.07, found: 353(M-H).

h. One-third of resin 2C was shaken with 3-nitrobenzoic acid in the same manner as described in 3a to yield resin 3CB. MS calcd. for $C_{14}H_{14}N_2O_9$: 354.07, found: 353(M-H).

i. One-third of resin 2C was shaken with 4-nitrobenzoic acid in the same manner as described in 3a to yield resin 3CC. MS calcd. for $C_{14}H_{14}N_2O_9$: 354.07, found: 353(M-H).

STEP 4. Reduction of Nitro Groups to Amines a. Resin 3AA was shaken with tin dichloride dihydrate (2.0 M, 20 ml) in DMF at room temperature overnight. The resin was washed with DMF (5×10 ml), methanol (3×10 ml), DMF (3×10 ml), methanol (3×10 ml), DCM (3×10 ml), methanol (3×10 ml), and air dried. A small sample (~50 mg) of the resulting resin 4AA was treated with TFA/water (95/5, 1.0 ml) for 1 hour at room temperature. The solution was collected via filtration. The resin was washed with acetic acid (3×1 ml). The combined solution was lyophilized. The residue was analyzed by mass spectrometry. MS calcd. for $C_{11}H_{12}N_2O_5$: 252.07, found: 251(M-H).

b. Resin 3AB was treated in the same manner as described in 4a to yield 4AB. MS calcd. for $C_{11}H_{12}N_2O_5$: 252.07, found: 251(M-H).

c. Resin 3AC was treated in the same manner as described in 4a to yield 4AC. MS calcd. for $C_{11}H_{12}N_2O_5$: 252.07, found: 251(M-H).

d. Resin 3BA was treated in the same manner as described in 4a to yield 4BA. MS calcd. for $C_{12}H_{14}N_2O_5$: 310.08, found: 309(M-H).

e. Resin 3BB was treated in the same manner as described in 4a to yield 4BB. MS calcd. for $C_{12}H_{14}N_2O_5$: 310.08, found: 309(M-H).

f. Resin 3BC was treated in the same manner as described in 4a to yield 4BC. MS calcd. for $C_{12}H_{14}N_2O_5$: 310.08, found 309(M-H).

g. Resin 3CA was treated in the same manner as described in 4a to yield 4CA. MS calcd. for $C_{12}H_{14}N_2O_5$: 324.10, found 323(M-H).

h. Resin 3CB was treated in the same manner as described in 4a to yield 4CB. MS calcd. for $C_{12}H_{14}N_2O_5$: 324.10, found 323(M-H).

i. Resin 3CC was treated in the same manner as described in 4a to yield 4CC. MS calcd. for $C_{12}H_{14}N_2O_5$: 324.10, found 323(M-H).

STEP 5. Coupling of Carboxylic Acids on to Resin and TFA Cleavage a. Resin 4AA was divided into 7 equal portions.

Portion A was shaken with acetic anhydride (A) (0.24 ml, 2.5 mmol), DIEA (0.87 ml, 5.0 mmol) and DMAP (10 mg) in DMF (5.0 ml) at room temperature overnight. The resin was washed with DMF (3×5 ml), methanol (3×5 ml), DMF (3×5 ml), methanol (3×5 ml), DCM (3×5 ml), methanol (3×5 ml), and air dried. The resulted resin 5AAA was treated with TFA/water (95/5, 3.0 ml) for 1 hour at room temperature. The solution was collected via filtration. The resin was washed with acetic acid (3×5 ml). The combined was lyophilized to give the desired product 6AAA. Its purity and identity were assessed using HPLC-MS spectrometry.

Portion B was shaken with benzoic acid (B) (0.31 g, 2.5 mmol), DIC (0.47 ml, 3.0 mmol), DIEA (0.87 ml, 5.0 mmol) and DMAP (10 mg) in DMF (5.0 ml) at room temperature overnight. The resin was washed with DMF (3×5 ml), methanol (3×5 ml), DMF (3×5 ml), methanol (3×5 ml), DCM (3×5 ml), methanol (3×5 ml), and air dried. The resulting resin 5AAB was treated with TFA/water (95/5, 3.0 ml) for 1 hour at room temperature. The solution was collected via filtration. The resin was washed with acetic acid (3×5 ml). The combined solution was lyophilized to give the desired product 6AAB. Its purity and identity were assessed using HPLC-MS spectrometry.

Portion C was treated with decanoic acid (C) in the same manner as described for Portion B.

Portion D was treated with glutaric anhydride (D) in the same manner as described for Portion A.

Portion E was treated with heptanoyl chloride (E) in the same manner as described for Portion A.

Portion F was treated with heptanoyl chloride (F) in the same manner as described for Portion A.

Portion G was treated with heptanoyl chloride (G) in the same manner as described for Portion A.

b. Resin 4AB, 4AC, 4BA, 4BB, 4BC, 4CA, 4CB, and 4CC were treated using the same procedure as described in Step 5a.

The compounds made according to the above procedures are summarized in the following Table 1. In Table 1, it should be noted that compounds are identified with three-letter codes. Within these three-letter codes, the first letter codes for the first component piece, the second letter codes for the second component piece, and the third letter codes for third component piece. Such first, second and third component pieces are identified in the reaction scheme presented above in this example.

TABLE 1

REPRESENTATIVE COMPOUNDS ($R_1$ OF STRUCTURE (I) = HYDROXY)

| Cpd. No. | First Component | Second Component | Third Component | Formula | MW Calcd | MW found (M − H) |
|---|---|---|---|---|---|---|
| 6AAA | glycine t-butyl ester (A) | 2-nitrobenzoic acid (A) | acetic anhydride (A) | $C_{13}H_{14}N_2O_6$ | 294.3 | 293 |
| 6AAB | glycine t-butyl ester (A) | 2-nitrobenzoic acid (A) | benzoic acid (B) | $C_{18}H_{16}N_2O_6$ | 356.3 | 355 |
| 6AAC | glycine t-butyl ester (A) | 2-nitrobenzoic acid (A) | decanoic acid (C) | $C_{21}H_{30}N_2O_6$ | 406.5 | 405 |
| 6AAD | glycine t-butyl ester (A) | 2-nitrobenzoic acid (A) | glutaric anhydride (D) | $C_{16}H_{18}N_2O_8$ | 366.5 | 365 |

TABLE 1-continued

REPRESENTATIVE COMPOUNDS ($R_1$ OF STRUCTURE (I) = HYDROXY)

| Cpd. No. | First Component | Second Component | Third Component | Formula | MW Calcd | MW found (M − H) |
|---|---|---|---|---|---|---|
| 6AAE | glycine t-butyl ester (A) | 2-nitrobenzoic acid (A) | heptanoyl chloride (E) | $C_{18}H_{24}N_2O_6$ | 364.4 | 363 |
| 6AAF | glycine t-butyl ester (A) | 2-nitrobenzoic acid (A) | methyl sebacoyl chloride (F) | $C_{22}H_{30}N_2O_8$ | 450.5 | 449 |
| 6AAG | glycine t-butyl ester (A) | 2-nitrobenzoic acid (A) | methyl suberyl chloride (G) | $C_{20}H_{26}N_2O_8$ | 422.4 | 421 |
| 6ABA | glycine t-butyl ester (A) | 3-nitrobenzoic acid (B) | acetic anhydride (A) | $C_{13}H_{14}N_2O_6$ | 294.3 | 293 |
| 6ABB | glycine t-butyl ester (A) | 3-nitrobenzoic acid (B) | benzoic acid (B) | $C_{18}H_{16}N_2O_6$ | 356.3 | 355 |
| 6ABC | glycine t-butyl ester (A) | 3-nitrobenzoic acid (B) | decanoic acid (C) | $C_{21}H_{30}N_2O_6$ | 406.5 | 405 |
| 6ABD | glycine t-butyl ester (A) | 3-nitrobenzoic acid (B) | glutaric anhydride (D) | $C_{16}H_{18}N_2O_8$ | 366.3 | 365 |
| 6ABE | glycine t-butyl ester (A) | 3-nitrobenzoic acid (B) | heptanoyl chloride (E) | $C_{18}H_{24}N_2O_6$ | 364.4 | 363 |
| 6ABF | glycine t-butyl ester (A) | 3-nitrobenzoic acid (B) | methyl sebacoyl chloride (F) | $C_{22}H_{30}N_2O_8$ | 450.5 | 449 |
| 6ABG | glycine t-butyl ester (A) | 3-nitrobenzoic acid (B) | methyl suberyl chloride (G) | $C_{20}H_{26}N_2O_8$ | 422.4 | 421 |
| 6ACA | glycine t-butyl ester (A) | 4-nitrobenzoic acid (C) | acetic anhydride (A) | $C_{13}H_{14}N_2O_6$ | 294.3 | 293 |
| 6ACB | glycine t-butyl ester (A) | 4-nitrobenzoic acid (C) | benzoic acid (B) | $C_{18}H_{16}N_2O_6$ | 356.3 | 355 |
| 6ACC | glycine t-butyl ester (A) | 4-nitrobenzoic acid (C) | decanoic acid (C) | $C_{21}H_{30}N_2O_6$ | 406.5 | 405 |
| 6ACD | glycine t-butyl ester (A) | 4-nitrobenzoic acid (C) | glutaric anhydride (D) | $C_{16}H_{18}N_2O_8$ | 366.3 | 365 |
| 6ACE | glycine t-butyl ester (A) | 4-nitrobenzoic acid (C) | heptanoyl chloride (E) | $C_{18}H_{24}N_2O_6$ | 364.4 | 363 |
| 6ACF | glycine t-butyl ester (A) | 4-nitrobenzoic acid (C) | methyl sebacoyl chloride (F) | $C_{22}H_{30}N_2O_8$ | 450.5 | 449 |
| 6ACG | glycine t-butyl ester (A) | 4-nitrobenzoic acid (C) | methyl suberyl chloride (G) | $C_{20}H_{26}N_2O_8$ | 422.4 | 421 |
| 6BAA | aspartic acid di-t-butyl ester (B) | 2-nitrobenzoic acid (A) | acetic anhydride (A) | $C_{15}H_{16}N_2O_8$ | 352.3 | 351 |
| 6BAB | aspartic acid di-t-butyl ester (B) | 2-nitrobenzoic acid (A) | benzoic acid (B) | $C_{20}H_{18}N_2O_8$ | 414.4 | 413 |
| 6BAC | aspartic acid di-t-butyl ester (B) | 2-nitrobenzoic acid (A) | decanoic acid (C) | $C_{23}H_{32}N_2O_8$ | 464.5 | 464 |
| 6BAD | aspartic acid di-t-butyl ester (B) | 2-nitrobenzoic acid (A) | glutaric anhydride (D) | $C_{18}H_{20}N_2O_{10}$ | 424.4 | 423 |
| 6BAE | aspartic acid di-t-butyl ester (B) | 2-nitrobenzoic acid (A) | heptanoyl chloride (E) | $C_{20}H_{25}N_2O_8$ | 422.4 | 421 |
| 6BAF | aspartic acid di-t-butyl ester (B) | 2-nitrobenzoic acid (A) | methyl sebacoyl chloride (F) | $C_{24}H_{32}N_2O_{10}$ | 508.5 | 508 |
| 6BAG | aspartic acid di-t-butyl ester (B) | 2-nitrobenzoic acid (A) | methyl suberyl chloride (G) | $C_{22}H_{28}N_2O_{10}$ | 480.5 | 479 |
| 6BBA | aspartic acid di-t-butyl ester (B) | 3-nitrobenzoic acid (B) | acetic anhydride (A) | $C_{15}H_{16}N_2O_8$ | 352.3 | 351 |
| 6BBB | aspartic acid di-t-butyl ester (B) | 3-nitrobenzoic acid (B) | benzoic acid (B) | $C_{20}H_{18}N_2O_8$ | 414.4 | 413 |
| 6BBC | aspartic acid di-t-butyl ester (B) | 3-nitrobenzoic acid (B) | decanoic acid (C) | $C_{23}H_{32}N_2O_8$ | 464.5 | 423 |
| 6BBD | aspartic acid di-t-butyl ester (B) | 3-nitrobenzoic acid (B) | glutaric anhydride (D) | $C_{18}H_{20}N_2O_{10}$ | 424.4 | 423 |

TABLE 1-continued

REPRESENTATIVE COMPOUNDS ($R_1$ OF STRUCTURE (I) = HYDROXY)

| Cpd. No. | First Component | Second Component | Third Component | Formula | MW Calcd | MW found (M − H) |
|---|---|---|---|---|---|---|
| 6BBE | aspartic acid di-t-butyl ester (B) | 3-nitrobenzoic acid (B) | heptanoyl chloride (E) | $C_{20}H_{26}N_2O_8$ | 422.4 | 421 |
| 6BBF | aspartic acid di-t-butyl ester (B) | 3-nitrobenzoic acid (B) | methyl sebacoyl chloride (F) | $C_{24}H_{32}N_2O_{10}$ | 508.5 | 508 |
| 6BBG | aspartic acid di-t-butyl ester (B) | 3-nitrobenzoic acid (B) | methyl suberyl chloride (G) | $C_{22}H_{28}N_2O_{10}$ | 480.5 | 479 |
| 6BCA | aspartic acid di-t-butyl ester (B) | 4-nitrobenzoic acid (C) | acetic anhydride (A) | $C_{15}H_{16}N_2O_8$ | 352.3 | 351 |
| 6BCB | aspartic acid di-t-butyl ester (B) | 4-nitrobenzoic acid (C) | benzoic acid (B) | $C_{20}H_{18}N_2O_8$ | 414.4 | 413 |
| 6BCC | aspartic acid di-t-butyl ester (B) | 4-nitrobenzoic acid (C) | decanoic acid (C) | $C_{23}H_{32}N_2O_8$ | 464.5 | 464 |
| 6BCD | aspartic acid di-t-butyl ester (B) | 4-nitrobenzoic acid (C) | glutaric anhydride (D) | $C_{18}H_{20}N_2O_{10}$ | 424.4 | 423 |
| 6BCE | aspartic acid di-t-butyl ester (B) | 4-nitrobenzoic acid (C) | heptanoyl chloride (E) | $C_{20}H_{26}N_2O_8$ | 422.4 | 421 |
| 6BCF | aspartic acid di-t-butyl ester (B) | 4-nitrobenzoic acid (C) | methyl sebacoyl chloride (F) | $C_{24}H_{32}N_2O_{10}$ | 508.5 | 508 |
| 6BCG | aspartic acid di-t-butyl ester (B) | 4-nitrobenzoic acid (C) | methyl suberyl chloride (G) | $C_{22}H_{28}N_2O_{10}$ | 480.5 | 479 |
| 6CAA | glutaric acid di-t-butyl ester (C) | 2-nitrobenzoic acid (A) | acetic anhydride (A) | $C_{16}H_{18}N_2O_8$ | 366.3 | 365 |
| 6CAB | glutaric acid di-t-butyl ester (C) | 2-nitrobenzoic acid (A) | benzoic acid (B) | $C_{21}H_{20}N_2O_8$ | 428.4 | 427 |
| 6CAC | glutaric acid di-t-butyl ester (C) | 2-nitrobenzoic acid (A) | decanoic acid (C) | $C_{24}H_{34}N_2O_8$ | 478.5 | 478 |
| 6CAD | glutaric acid di-t-butyl ester (C) | 2-nitrobenzoic acid (A) | glutaric anhydride (D) | $C_{19}H_{22}N_2O_{10}$ | 438.4 | 437 |
| 6CAE | glutaric acid di-t-butyl ester (C) | 2-nitrobenzoic acid (A) | heptanoyl chloride (E) | $C_{21}H_{28}N_2O_8$ | 436.6 | 435 |
| 6CAF | glutaric acid di-t-butyl ester (C) | 2-nitrobenzoic acid (A) | methyl sebacoyl chloride (F) | $C_{25}H_{34}N_2O_{10}$ | 522.6 | 522 |
| 6CAG | glutaric acid di-t-butyl ester (C) | 2-nitrobenzoic acid (A) | methyl suberyl chloride (G) | $C_{23}H_{30}N_2O_{10}$ | 494.5 | 493 |
| 6CBA | glutaric acid di-t-butyl ester (C) | 3-nitrobenzoic acid (B) | acetic anhydride (A) | $C_{16}H_{18}N_2O_8$ | 366.3 | 365 |
| 6CBB | glutaric acid di-t-butyl ester (C) | 3-nitrobenzoic acid (B) | benzoic acid (B) | $C_{21}H_{20}N_2O_8$ | 428.4 | 427 |
| 6CBC | glutaric acid di-t-butyl ester (C) | 3-nitrobenzoic acid (B) | decanoic acid (C) | $C_{24}H_{34}N_2O_8$ | 478.5 | 478 |
| 6CBD | glutaric acid di-t-butyl ester (C) | 3-nitrobenzoic acid (B) | glutaric anhydride (D) | $C_{19}H_{22}N_2O_{10}$ | 438.4 | 437 |
| 6CBE | glutaric acid di-t-butyl ester (C) | 3-nitrobenzoic acid (B) | heptanoyl chloride (E) | $C_{21}H_{28}N_2O_8$ | 436.5 | 435 |
| 6CBF | glutaric acid di-t-butyl ester (C) | 3-nitrobenzoic acid (B) | methyl sebacoyl chloride (F) | $C_{25}H_{34}N_2O_{10}$ | 522.6 | 522 |
| 6CBG | glutaric acid di-t-butyl ester (C) | 3-nitrobenzoic acid (B) | methyl suberyl chloride (G) | $C_{23}H_{30}N_2O_{10}$ | 494.5 | 493 |

TABLE 1-continued

REPRESENTATIVE COMPOUNDS ($R_1$ OF STRUCTURE (I) = HYDROXY)

| Cpd. No. | First Component | Second Component | Third Component | Formula | MW Calcd | MW found (M − H) |
|---|---|---|---|---|---|---|
| 6CCA | glutaric acid di-t-butyl ester (C) | 4-nitrobenzoic acid (C) | acetic anhydride (A) | $C_{16}H_{18}N_2O_8$ | 366.3 | 365 |
| 6CCB | glutaric acid di-t-butyl ester (C) | 4-nitrobenzoic acid (C) | benzoic acid (B) | $C_{21}H_{20}N_2O_8$ | 428.4 | 427 |
| 6CCC | glutaric acid di-t-butyl ester (C) | 4-nitrobenzoic acid (C) | decanoic acid (C) | $C_{24}H_{34}N_2O_8$ | 478.5 | 478 |
| 6CCD | glutaric acid di-t-butyl ester (C) | 4-nitrobenzoic acid (C) | glutaric anhydride (D) | $C_{19}H_{22}N_2O_{10}$ | 438.4 | 437 |
| 6CCE | glutaric acid di-t-butyl ester (C) | 4-nitrobenzoic acid (C) | heptanoyl chloride (E) | $C_{21}H_{28}N_2O_8$ | 436.5 | 435 |
| 6CCF | glutaric acid di-t-butyl ester (C) | 4-nitrobenzoic acid (C) | methyl sebacoyl chloride (F) | $C_{25}H_{34}N_2O_{10}$ | 522.6 | 522 |
| 6CCG | glutaric acid di-t-butyl ester (C) | 4-nitrobenzoic acid (C) | methyl suberyl chloride (G) | $C_{23}H_{30}N_2O_{10}$ | 494.5 | 493 |

Example 2

Synthesis of Representative Compounds of Structure (I)

Using the same procedures as illustrated in Example 1, additional representative compounds were prepared using glycine methyl ester (A) or glycinamide (B) as the first component. The corresponding compounds are listed below in Table 2.

TABLE 2

REPRESENTATIVE COMPOUNDS ($R_1$ OF STRUCTURE (I) = METHOXY OR AMINO)

| Cpd. No. | First Component | Second Component | Third Component | Formula | MW Calcd | MW found (M − H) |
|---|---|---|---|---|---|---|
| 7AAA | glycine methyl ester (A) | 3-nitrobenzoic acid (A) | glutaric anhydride (A) | $C_{17}H_{20}N_2O_8$ | 380.4 | 381 |
| 7AAB | glycine methyl ester (A) | 3-nitrobenzoic acid (A) | heptanoyl chloride (B) | $C_{19}H_{26}N_2O_6$ | 378.4 | 379 |
| 7AAC | glycine methyl ester (A) | 3-nitrobenzoic acid (A) | decanoic acid (C) | $C_{22}H_{32}N_2O_6$ | 420.5 | 421 |
| 7AAD | glycine methyl ester (A) | 3-nitrobenzoic acid (A) | methyl suberyl chloride (D) | $C_{21}H_{28}N_2O_8$ | 436.5 | 437 |
| 7AAE | glycine methyl ester (A) | 3-nitrobenzoic acid (A) | methyl sebacoyl chloride (E) | $C_{23}H_{32}N_2O_8$ | 464.5 | 465 |
| 7ABA | glycine methyl ester (A) | 4-nitrobenzoic acid (B) | glutaric anhydride (A) | $C_{17}H_{20}N_2O_8$ | 380.4 | 381 |
| 7ABB | glycine methyl ester (A) | 4-nitrobenzoic acid (B) | heptanoyl chloride (B) | $C_{19}H_{26}N_2O_6$ | 378.4 | 379 |
| 7ABC | glycine methyl ester (A) | 4-nitrobenzoic acid (B) | decanoic acid (C) | $C_{22}H_{32}N_2O_6$ | 420.5 | 421 |
| 7ABD | glycine methyl ester (A) | 4-nitrobenzoic acid (B) | methyl suberyl chloride (D) | $C_{21}H_{28}N_2O_8$ | 436.5 | 437 |
| 7ABE | glycine methyl ester (A) | 4-nitrobenzoic acid (B) | methyl sebacoyl chloride (E) | $C_{23}H_{32}N_2O_8$ | 464.5 | 465 |
| 7BAA | glycinamide (B) | 3-nitrobenzoic acid (A) | glutaric anhydride (A) | $C_{16}H_{19}N_3O_7$ | 365.3 | 366 |

TABLE 2-continued

REPRESENTATIVE COMPOUNDS ($R_1$ OF STRUCTURE (I) = METHOXY OR AMINO)

| Cpd. No. | First Component | Second Component | Third Component | Formula | MW Calcd | MW found (M − H) |
|---|---|---|---|---|---|---|
| 7BAB | glycinamide (B) | 3-nitrobenzoic acid (A) | heptanoyl chloride (B) | $C_{18}H_{25}N_3O_5$ | 363.4 | 364 |
| 7BAC | glycinamide (B) | 3-nitrobenzoic acid (A) | decanoic acid (C) | $C_{21}H_{31}N_3O_5$ | 405.5 | 406 |
| 7BAD | glycinamide (B) | 3-nitrobenzoic acid (A) | methyl suberyl chloride (D) | $C_{20}H_{27}N_3O_7$ | 421.4 | 422 |
| 7BAE | glycinamide (B) | 3-nitrobenzoic acid (A) | methyl sebacoyl chloride (E) | $C_{22}H_{31}N_3O_7$ | 449.5 | 450 |
| 7BBA | glycinamide (B) | 4-nitrobenzoic acid (B) | glutaric anhydride (A) | $C_{16}H_{19}N_3O_7$ | 365.3 | 366 |
| 7BBB | glycinamide (B) | 4-nitrobenzoic acid (B) | heptanoyl chloride (B) | $C_{18}H_{25}N_3O_5$ | 363.4 | 364 |
| 7BBC | glycinamide (B) | 4-nitrobenzoic acid (B) | decanoic acid (C) | $C_{21}H_{31}N_3O_5$ | 405.5 | 406 |
| 7BBD | glycinamide (B) | 4-nitrobenzoic acid (B) | methyl suberyl chloride (D) | $C_{20}H_{27}N_3O_7$ | 421.4 | 422 |
| 7BBE | glycinamide (B) | 4-nitrobenzoic acid (B) | methyl sebacoyl chloride (E) | $C_{22}H_{31}N_3O_7$ | 449.5 | 450 |

Example 3

Synthesis of Representative Compounds of Structure (I)

Using the same procedures as illustrated in Example 1, additional representative compounds were prepared using alanine benzyl ester (A), valine benzyl ester (B), leucine benzyl ester (C) or phenylalanine benzyl ester (D) as the first component. The corresponding products are listed below in Table 3.

TABLE 3

REPRESENTATIVE COMPOUNDS ($R_1$ OF STRUCTURE (I) = BNO)

| Cpd. No. | First Component | Second Component | Third Component | Formula | MW Calcd | MW found (M − H) |
|---|---|---|---|---|---|---|
| 8AAA | alanine benzyl ester (A) | 3-nitrobenzoic acid (A) | glutaric anhydride (A) | $C_{26}H_{30}N_2O_8$ | 498.5 | 499 |
| 8AAB | alanine benzyl ester (A) | 3-nitrobenzoic acid (A) | heptanoyl chloride (B) | $C_{28}H_{36}N_2O_6$ | 496.6 | 497 |
| 8AAC | alanine benzyl ester (A) | 3-nitrobenzoic acid (A) | decanoic acid (C) | $C_{31}H_{42}N_2O_6$ | 538.7 | 539 |
| 8AAD | alanine benzyl ester (A) | 3-nitrobenzoic acid (A) | methyl suberyl chloride (D) | $C_{30}H_{38}N_2O_8$ | 554.6 | 555 |
| 8AAE | alanine benzyl ester (A) | 3-nitrobenzoic acid (A) | methyl sebacoyl chloride (E) | $C_{32}H_{42}N_2O_8$ | 582.7 | 583 |
| 8ABA | alanine benzyl ester (A) | 4-nitrobenzoic acid (B) | glutaric anhydride (A) | $C_{20}H_{26}N_2O_8$ | 422.4 | 423 |
| 8ABB | alanine benzyl ester (A) | 4-nitrobenzoic acid (B) | heptanoyl chloride (B) | $C_{22}H_{32}N_2O_6$ | 420.5 | 421 |
| 8ABC | alanine benzyl ester (A) | 4-nitrobenzoic acid (B) | decanoic acid (C) | $C_{25}H_{38}N_2O_6$ | 462.6 | 463 |
| 8ABD | alanine benzyl ester (A) | 4-nitrobenzoic acid (B) | methyl suberyl chloride (D) | $C_{24}H_{34}N_2O_8$ | 478.5 | 479 |

TABLE 3-continued

REPRESENTATIVE COMPOUNDS ($R_1$ OF STRUCTURE (I) = BNO)

| Cpd. No. | First Component | Second Component | Third Component | Formula | MW Calcd | MW found (M – H) |
|---|---|---|---|---|---|---|
| 8ABE | alanine benzyl ester (A) | 4-nitrobenzoic acid (B) | methyl sebacoyl chloride (E) | $C_{26}H_{38}N_2O_8$ | 506.6 | 507 |
| 8BAA | valine benzyl ester (B) | 3-nitrobenzoic acid (A) | glutaric anhydride (A) | $C_{27}H_{32}N_2O_8$ | 512.6 | 513 |
| 8BAB | valine benzyl ester (B) | 3-nitrobenzoic acid (A) | heptanoyl chloride (B) | $C_{29}H_{38}N_2O_6$ | 510.6 | 511 |
| 8BAC | valine benzyl ester (B) | 3-nitrobenzoic acid (A) | decanoic acid (C) | $C_{32}H_{44}N_2O_6$ | 552.7 | 553 |
| 8BAD | valine benzyl ester (B) | 3-nitrobenzoic acid (A) | methyl suberyl chloride (D) | $C_{31}H_{40}N_2O_8$ | 568.7 | 569 |
| 8BAE | valine benzyl ester (B) | 4-nitrobenzoic acid (B) | methyl sebacoyl chloride (E) | $C_{33}H_{44}N_2O_8$ | 596.7 | 597 |
| 8BBA | valine benzyl ester (B) | 4-nitrobenzoic acid (B) | glutaric anhydride (A) | $C_{20}H_{26}N_2O_8$ | 422.4 | 423 |
| 8BBB | valine benzyl ester (B) | 4-nitrobenzoic acid (B) | heptanoyl chloride (B) | $C_{22}H_{32}N_2O_6$ | 420.5 | 421 |
| 8BBC | valine benzyl ester (B) | 4-nitrobenzoic acid (B) | decanoic acid (C) | $C_{25}H_{38}N_2O_6$ | 462.6 | 463 |
| 8BBD | valine benzyl ester (B) | 4-nitrobenzoic acid (B) | methyl suberyl chloride (D) | $C_{24}H_{34}N_2O_8$ | 478.5 | 479 |
| 8BBE | valine benzyl ester (B) | 4-nitrobenzoic acid (B) | methyl sebacoyl chloride (E) | $C_{26}H_{38}N_2O_8$ | 506.6 | 507 |
| 8CAA | leucine benzyl ester (C) | 3-nitrobenzoic acid (A) | glutaric anhydride (A) | $C_{27}H_{32}N_2O_8$ | 512.6 | 513 |
| 8CAB | leucine benzyl ester (C) | 3-nitrobenzoic acid (A) | heptanoyl chloride (B) | $C_{29}H_{38}N_2O_6$ | 510.6 | 511 |
| 8CAC | leucine benzyl ester (C) | 3-nitrobenzoic acid (A) | decanoic acid (C) | $C_{32}H_{44}N_2O_6$ | 552.7 | 553 |
| 8CAD | leucine benzyl ester (C) | 3-nitrobenzoic acid (A) | methyl suberyl chloride (D) | $C_{31}H_{40}N_2O_8$ | 568.7 | 569 |
| 8CAE | leucine benzyl ester (C) | 3-nitrobenzoic acid (A) | methyl sebacoyl chloride (E) | $C_{33}H_{44}N_2O_8$ | 596.7 | 597 |
| 8CBA | leucine benzyl ester (C) | 4-nitrobenzoic acid (B) | glutaric anhydride (A) | $C_{23}H_{24}N_2O_8$ | 456.6 | 457 |
| 8CBB | leucine benzyl ester (C) | 4-nitrobenzoic acid (B) | heptanoyl chloride (B) | $C_{25}H_{30}N_2O_6$ | 454.5 | 455 |
| 8CBC | leucine benzyl ester (C) | 4-nitrobenzoic acid (B) | decanoic acid (C) | $C_{28}H_{36}N_2O_6$ | 496.6 | 497 |
| 8CBD | leucine benzyl ester (C) | 4-nitrobenzoic acid (B) | methyl suberyl chloride (D) | $C_{27}H_{32}N_2O_8$ | 512.6 | 513 |
| 8CBE | leucine benzyl ester (C) | 4-nitrobenzoic acid (B) | methyl sebacoyl chloride (E) | $C_{29}H_{36}N_2O_8$ | 540.6 | 541 |
| 8DBA | phenylalanine benzyl ester (D) | 4-nitrobenzoic acid (B) | glutaric anhydride (A) | $C_{30}H_{30}N_2O_8$ | 546.6 | 547 |
| 8DBB | phenylalanine benzyl ester (D) | 4-nitrobenzoic acid (B) | heptanoyl chloride (B) | $C_{32}H_{36}N_2O_6$ | 544.6 | 545 |
| 8DBC | phenylalanine benzyl ester (D) | 4-nitrobenzoic acid (B) | decanoic acid (C) | $C_{35}H_{42}N_2O_6$ | 586.7 | 587 |
| 8DBD | phenylalanine benzyl ester (D) | 4-nitrobenzoic acid (B) | methyl suberyl chloride (D) | $C_{34}H_{38}N_2O_8$ | 602.7 | 603 |
| 8DBE | phenylalanine benzyl ester (D) | 4-nitrobenzoic acid (B) | methyl sebacoyl chloride (E) | $C_{36}H_{42}N_2O_8$ | 630.7 | 631 |

Example 4

Synthesis of Representative Compounds of Structure (I)

Each of the compounds of Example 3 was divided into two portions. One portion was treated with hydrogen (10 psi) in the presence of 10% Palladium on activated carbon (15 mg) in acetic acid/methanol (1/4, 5 ml) at room temperature overnight. The Pd/C was removed by filtration and washed with acetic acid (3×5 ml). This resulted in the conversion of the benzyl ester ($R_1$=BnO) to the corresponding acid ($R_1$=OH). The resulting compounds are summarized in Table 4.

TABLE 4

REPRESENTATIVE COMPOUNDS ($R_1$ OF STRUCTURE (I) = OH)

| Cpd. No. | First Component | Second Component | Third Component | Formula | MW Calcd | MW found (M − H) |
|---|---|---|---|---|---|---|
| 9AAA | alanine benzyl ester (A) | 3-nitrobenzoic acid (A) | glutaric anhydride (A) | $C_{17}H_{20}N_2O_8$ | 380.4 | 381 |
| 9AAB | alanine benzyl ester (A) | 3-nitrobenzoic acid (A) | heptanoyl chloride (B) | $C_{19}H_{26}N_2O_6$ | 378.4 | 379 |
| 9AAC | alanine benzyl ester (A) | 3-nitrobenzoic acid (A) | decanoic acid (C) | $C_{22}H_{32}N_2O_6$ | 420.5 | 421 |
| 9AAD | alanine benzyl ester (A) | 3-nitrobenzoic acid (A) | methyl suberyl chloride (D) | $C_{21}H_{28}N_2O_8$ | 436.5 | 437 |
| 9AAE | alanine benzyl ester (A) | 3-nitrobenzoic acid (A) | methyl sebacoyl chloride (E) | $C_{23}H_{32}N_2O_8$ | 464.5 | 465 |
| 9ABA | alanine benzyl ester (A) | 4-nitrobenzoic acid (B | glutaric anhydride (A) | $C_{24}H_{26}N_2O_8$ | 470.5 | 471 |
| 9ABB | alanine benzyl ester (A) | 4-nitrobenzoic acid (B | heptanoyl chloride (B) | $C_{26}H_{32}N_2O_6$ | 468.5 | 469 |
| 9ABC | alanine benzyl ester (A) | 4-nitrobenzoic acid (B | decanoic acid (C) | $C_{29}H_{38}N_2O_6$ | 510.6 | 511 |
| 9ABD | alanine benzyl ester (A) | 4-nitrobenzoic acid (B | methyl suberyl chloride (D) | $C_{28}H_{34}N_2O_8$ | 526.6 | 527 |
| 9ABE | alanine benzyl ester (A) | 4-nitrobenzoic acid (B | methyl sebacoyl chloride (E) | $C_{30}H_{38}N_2O_8$ | 554.6 | 555 |
| 9BAA | valine benzyl ester (B) | 3-nitrobenzoic acid (A) | glutaric anhydride (A) | $C_{17}H_{20}N_2O_8$ | 380.4 | 381 |
| 9BAB | valine benzyl ester (B) | 3-nitrobenzoic acid (A) | heptanoyl chloride (B) | $C_{19}H_{26}N_2O_6$ | 378.4 | 379 |
| 9BAC | valine benzyl ester (B) | 3-nitrobenzoic acid (A) | decanoic acid (C) | $C_{22}H_{32}N_2O_6$ | 420.5 | 421 |
| 9BAD | valine benzyl ester (B) | 3-nitrobenzoic acid (A) | methyl suberyl chloride (D) | $C_{21}H_{28}N_2O_8$ | 436.5 | 437 |
| 9BAE | valine benzyl ester (B) | 3-nitrobenzoic acid (A) | methyl sebacoyl chloride (E) | $C_{23}H_{32}N_2O_8$ | 464.5 | 465 |
| 9BBA | valine benzyl ester (B) | 4-nitrobenzoic acid (B) | glutaric anhydride (A) | $C_{24}H_{26}N_2O_8$ | 470.5 | 471 |
| 9BBB | valine benzyl ester (B) | 4-nitrobenzoic acid (B) | heptanoyl chloride (B) | $C_{26}H_{32}N_2O_6$ | 468.5 | 469 |
| 9BBC | valine benzyl ester (B) | 4-nitrobenzoic acid (B) | decanoic acid (C) | $C_{29}H_{38}N_2O_6$ | 510.6 | 511 |
| 9BBD | valine benzyl ester (B) | 4-nitrobenzoic acid (B) | methyl suberyl chloride (D) | $C_{28}H_{34}N_2O_8$ | 526.6 | 527 |
| 9BBE | valine benzyl ester (B) | 4-nitrobenzoic acid (B) | methyl sebacoyl chloride (E) | $C_{30}H_{38}N_2O_8$ | 554.6 | 555 |
| 9CAA | leucine benzyl ester (C) | 3-nitrobenzoic acid (A) | glutaric anhydride (A) | $C_{19}H_{24}N_2O_8$ | 408.4 | 409 |
| 9CAB | leucine benzyl ester (C) | 3-nitrobenzoic acid (A) | heptanoyl chloride (B) | $C_{21}H_{30}N_2O_6$ | 406.5 | 407 |
| 9CAC | leucine benzyl ester (C) | 3-nitrobenzoic acid (A) | decanoic acid (C) | $C_{24}H_{36}N_2O_6$ | 448.6 | 449 |
| 9CAD | leucine benzyl ester (C) | 3-nitrobenzoic acid (A) | methyl suberyl chloride (D) | $C_{23}H_{32}N_2O_8$ | 464.5 | 465 |
| 9CAE | leucine benzyl ester (C) | 3-nitrobenzoic acid (A) | methyl sebacoyl chloride (E) | $C_{25}H_{36}N_2O_8$ | 492.6 | 493 |
| 9CBA | leucine benzyl ester (C) | 4-nitrobenzoic acid (B) | glutaric anhydride (A) | $C_{26}H_{30}N_2O_8$ | 498.5 | 499 |
| 9CBB | leucine benzyl ester (C) | 4-nitrobenzoic acid (B) | heptanoyl chloride (B) | $C_{28}H_{36}N_2O_6$ | 496.6 | 497 |

TABLE 4-continued

REPRESENTATIVE COMPOUNDS ($R_1$ OF STRUCTURE (I) = OH)

| Cpd. No. | First Component | Second Component | Third Component | Formula | MW Calcd | MW found (M − H) |
|---|---|---|---|---|---|---|
| 9CBC | leucine benzyl ester (C) | 4-nitrobenzoic acid (B) | decanoic acid (C) | $C_{31}H_{42}N_2O_6$ | 538.7 | 539 |
| 9CBD | leucine benzyl ester (C) | 4-nitrobenzoic acid (B) | methyl suberyl chloride (D) | $C_{30}H_{38}N_2O_8$ | 554.6 | 555 |
| 9CBE | leucine benzyl ester (C) | 4-nitrobenzoic acid (B) | methyl sebacoyl chloride (E) | $C_{32}H_{42}N_2O_8$ | 582.7 | 583 |
| 9DBA | phenylalanine benzyl ester (D) | 4-nitrobenzoic acid (B) | glutaric anhydride (A) | $C_{19}H_{24}N_2O_8$ | 408.4 | 409 |
| 9DBB | phenylalanine benzyl ester (D) | 4-nitrobenzoic acid (B) | heptanoyl chloride (B) | $C_{21}H_{30}N_2O_6$ | 406.5 | 407 |
| 9DBC | phenylalanine benzyl ester (D) | 4-nitrobenzoic acid (B) | decanoic acid (C) | $C_{24}H_{36}N_2O_6$ | 448.6 | 449 |
| 9DBD | phenylalanine benzyl ester (D) | 4-nitrobenzoic acid (B) | methyl suberyl chloride (D) | $C_{23}H_{32}N_2O_8$ | 464.5 | 465 |
| 9DBE | phenylalanine benzyl ester (D) | 4-nitrobenzoic acid (B) | methyl sebacoyl chloride (E) | $C_{25}H_{36}N_2O_8$ | 492.6 | 493 |

Example 5

Synthesis of Representative Compounds of Structure (I)

Using the same procedures as illustrated in Example 1, additional representative compounds were prepared using leucine benzyl ester (A) or phenylalanine benzyl ester (B) as the first component, and using various second components to illustrate embodiments wherein the "A" moiety of structure (I) is other than a direct bond. The corresponding compounds are listed below in Table 5.

TABLE 5

REPRESENTATIVE COMPOUNDS ($R_1$ OF STRUCTURE (I) = BNO)

| Cpd. No. | First Component | Second Component | Third Component | Formula | MW Calcd | MW found (M − H) |
|---|---|---|---|---|---|---|
| 10AAA | Leucine benzyl ester (A) | 2-nitrophenyl-acetic acid (A) | glutaric anhydride (A) | $C_{28}H_{34}N_2O_8$ | 526.6 | 527 |
| 10AAB | Leucine benzyl ester (A) | 2-nitrophenyl-acetic acid (A) | heptanoyl chloride (B) | $C_{30}H_{40}N_2O_6$ | 524.7 | 525 |
| 10AAC | Leucine benzyl ester (A) | 2-nitrophenyl-acetic acid (A) | decanoic acid (C) | $C_{33}H_{46}N_2O_6$ | 566.7 | 567 |
| 10AAD | Leucine benzyl ester (A) | 2-nitrophenyl-acetic acid (A) | methyl suberyl chloride (D) | $C_{32}H_{42}N_2O_8$ | 582.7 | 583 |
| 10AAE | Leucine benzyl ester (A) | 2-nitrophenyl-acetic acid (A) | methyl sebacoyl chloride (E) | $C_{34}H_{46}N_2O_8$ | 610.7 | 611 |
| 10BAA | Phenylalanine benzyl ester (B) | 2-nitrophenyl-acetic acid (A) | glutaric anhydride (A) | $C_{31}H_{32}N_2O_8$ | 560.6 | 561 |
| 10BAB | Phenylalanine benzyl ester (B) | 2-nitrophenyl-acetic acid (A) | heptanoyl chloride (B) | $C_{33}H_{38}N_2O_6$ | 558.7 | 559 |

TABLE 5-continued

REPRESENTATIVE COMPOUNDS ($R_1$ OF STRUCTURE (I) = BNO)

| Cpd. No. | First Component | Second Component | Third Component | Formula | MW Calcd | MW found (M − H) |
|---|---|---|---|---|---|---|
| 10BAC | Phenylalanine benzyl ester (B) | 2-nitrophenyl-acetic acid (A) | decanoic acid (C) | $C_{36}H_{44}N_2O_6$ | 600.8 | 601 |
| 10BAD | Phenylalanine benzyl ester (B) | 2-nitrophenyl-acetic acid (A) | methyl suberyl chloride (D) | $C_{35}H_{40}N_2O_8$ | 616.7 | 617 |
| 10BAE | Phenylalanine benzyl ester (B) | 2-nitrophenyl-acetic acid (A) | methyl sebacoyl chloride (E) | $C_{37}H_{44}N_2O_8$ | 644.8 | 645 |
| 10ABA | Leucine benzyl ester (A) | 3-nitrophenyl-acetic acid (B) | glutaric anhydride (A) | $C_{28}H_{34}N_2O_8$ | 526.6 | 527 |
| 10ABB | Leucine benzyl ester (A) | 3-nitrophenyl-acetic acid (B) | heptanoyl chloride (B) | $C_{30}H_{40}N_2O_6$ | 524.7 | 525 |
| 10ABC | Leucine benzyl ester (A) | 3-nitrophenyl-acetic acid (B) | decanoic acid (C) | $C_{33}H_{46}N_2O_6$ | 566.7 | 567 |
| 10ABD | Leucine benzyl ester (A) | 3-nitrophenyl-acetic acid (B) | methyl suberyl chloride (D) | $C_{32}H_{42}N_2O_8$ | 582.7 | 583 |
| 10ABE | Leucine benzyl ester (A) | 3-nitrophenyl-acetic acid (B) | methyl sebacoyl chloride (E) | $C_{34}H_{46}N_2O_8$ | 610.7 | 611 |
| 10BBA | Phenylalanine benzyl ester (B) | 3-nitrophenyl-acetic acid (B) | glutaric anhydride (A) | $C_{31}H_{32}N_2O_8$ | 560.6 | 561 |
| 10BBB | Phenylalanine benzyl ester (B) | 3-nitrophenyl-acetic acid (B) | heptanoyl chloride (B) | $C_{33}H_{38}N_2O_6$ | 558.7 | 559 |
| 10BBC | Phenylalanine benzyl ester (B) | 3-nitrophenyl-acetic acid (B) | decanoic acid (C) | $C_{36}H_{44}N_2O_6$ | 600.8 | 601 |
| 10BBD | Phenylalanine benzyl ester (B) | 3-nitrophenyl-acetic acid (B) | methyl suberyl chloride (D) | $C_{35}H_{40}N_2O_8$ | 616.7 | 617 |
| 10BBE | Phenylalanine benzyl ester (B) | 3-nitrophenyl-acetic acid (B) | methyl sebacoyl chloride (E) | $C_{37}H_{44}N_2O_8$ | 644.8 | 645 |
| 10ACA | Leucine benzyl ester (A) | 4-nitrophenyl-acetic acid (C) | glutaric anhydride (A) | $C_{28}H_{34}N_2O_8$ | 526.6 | 527 |
| 10ACB | Leucine benzyl ester (A) | 4-nitrophenyl-acetic acid (C) | heptanoyl chloride (B) | $C_{30}H_{40}N_2O_6$ | 524.7 | 525 |
| 10ACC | Leucine benzyl ester (A) | 4-nitrophenyl-acetic acid (C) | decanoic acid (C) | $C_{33}H_{46}N_2O_6$ | 566.7 | 567 |
| 10ACD | Leucine benzyl ester (A) | 4-nitrophenyl-acetic acid (C) | methyl suberyl chloride (D) | $C_{32}H_{42}N_2O_8$ | 582.7 | 583 |
| 10ACE | Leucine benzyl ester (A) | 4-nitrophenyl-acetic acid (C) | methyl sebacoyl chloride (E) | $C_{34}H_{46}N_2O_8$ | 610.7 | 611 |
| 10BCA | Phenylalanine benzyl ester (B) | 4-nitrophenyl-acetic acid (C) | glutaric anhydride (A) | $C_{31}H_{32}N_2O_8$ | 560.6 | 561 |
| 10BCB | Phenylalanine benzyl ester (B) | 4-nitrophenyl-acetic acid (C) | heptanoyl chloride (B) | $C_{33}H_{38}N_2O_6$ | 558.7 | 559 |
| 10BCC | Phenylalanine benzyl ester (B) | 4-nitrophenyl-acetic acid (C) | decanoic acid (C) | $C_{36}H_{44}N_2O_6$ | 600.8 | 601 |
| 10BCD | Phenylalanine benzyl ester (B) | 4-nitrophenyl-acetic acid (C) | methyl suberyl chloride (D) | $C_{35}H_{40}N_2O_8$ | 616.7 | 617 |
| 10BCE | Phenylalanine benzyl ester (B) | 4-nitrophenyl-acetic acid (C) | methyl sebacoyl chloride (E) | $C_{37}H_{44}N_2O_8$ | 644.8 | 645 |
| 10ADA | Leucine benzyl ester (A) | 2-nitrophenoxy-acetic acid (D) | glutaric anhydride (A) | $C_{28}H_{34}N_2O_9$ | 542.6 | 543 |

TABLE 5-continued

REPRESENTATIVE COMPOUNDS ($R_1$ OF STRUCTURE (I) = BNO)

| Cpd. No. | First Component | Second Component | Third Component | Formula | MW Calcd | MW found (M − H) |
|---|---|---|---|---|---|---|
| 10ADD | Leucine benzyl ester (A) | 2-nitrophenoxy-acetic acid (D) | methyl suberyl chloride (D) | $C_{32}H_{42}N_2O_9$ | 598.7 | 599 |
| 10ADE | Leucine benzyl ester (A) | 2-nitrophenoxy-acetic acid (D) | methyl sebacoyl chloride (E) | $C_{34}H_{46}N_2O_9$ | 626.7 | 627 |
| 10BDA | Phenylalanine benzyl ester (B) | 2-nitrophenoxy-acetic acid (D) | glutaric anhydride (A) | $C_{31}H_{32}N_2O_9$ | 576.6 | 577 |
| 10BDB | Phenylalanine benzyl ester (B) | 2-nitrophenoxy-acetic acid (D) | heptanoyl chloride (B) | $C_{33}H_{38}N_2O_7$ | 574.7 | 575 |
| 10BDC | Phenylalanine benzyl ester (B) | 2-nitrophenoxy-acetic acid (D) | decanoic acid (C) | $C_{36}H_{44}N_2O_7$ | 616.8 | 617 |
| 10AEA | Leucine benzyl ester (A) | 3-nitrophenoxy-acetic acid (E) | glutaric anhydride (A) | $C_{28}H_{34}N_2O_9$ | 542.6 | 543 |
| 10AEB | Leucine benzyl ester (A) | 3-nitrophenoxy-acetic acid (E) | heptanoyl chloride (B) | $C_{30}H_{40}N_2O_7$ | 540.7 | 541 |
| 10AEC | Leucine benzyl ester (A) | 3-nitrophenoxy-acetic acid (E) | decanoic acid (C) | $C_{33}H_{46}N_2O_7$ | 582.7 | 583 |
| 10AED | Leucine benzyl ester (A) | 3-nitrophenoxy-acetic acid (E) | methyl suberyl chloride (D) | $C_{32}H_{42}N_2O_9$ | 598.7 | 599 |
| 10AEE | Leucine benzyl ester (A) | 3-nitrophenoxy-acetic acid (E) | methyl sebacoyl chloride (E) | $C_{34}H_{46}N_2O_9$ | 626.7 | 627 |
| 10BEA | Phenylalanine benzyl ester (B) | 3-nitrophenoxy-acetic acid (E) | glutaric anhydride (A) | $C_{31}H_{32}N_2O_9$ | 576.6 | 577 |
| 10BEB | Phenylalanine benzyl ester (B) | 3-nitrophenoxy-acetic acid (E) | heptanoyl chloride (B) | $C_{33}H_{38}N_2O_7$ | 574.7 | 575 |
| 10BEC | Phenylalanine benzyl ester (B) | 3-nitrophenoxy-acetic acid (E) | decanoic acid (C) | $C_{36}H_{44}N_2O_7$ | 616.8 | 617 |
| 10BED | Phenylalanine benzyl ester (B) | 3-nitrophenoxy-acetic acid (E) | methyl suberyl chloride (D) | $C_{35}H_{40}N_2O_9$ | 632.7 | 633 |
| 10BEE | Phenylalanine benzyl ester (B) | 3-nitrophenoxy-acetic acid (E) | methyl sebacoyl chloride (E) | $C_{37}H_{44}N_2O_9$ | 660.8 | 661 |
| 10AFA | Leucine benzyl ester (A) | 4-nitrophenoxy-acetic acid (F) | glutaric anhydride (A) | $C_{28}H_{34}N_2O_9$ | 542.6 | 543 |
| 10AFB | Leucine benzyl ester (A) | 4-nitrophenoxy-acetic acid (F) | heptanoyl chloride (B) | $C_{30}H_{40}N_2O_7$ | 540.7 | 541 |
| 10AFC | Leucine benzyl ester (A) | 4-nitrophenoxy-acetic acid (F) | decanoic acid (C) | $C_{33}H_{46}N_2O_7$ | 582.7 | 583 |
| 10AFD | Leucine benzyl ester (A) | 4-nitrophenoxy-acetic acid (F) | methyl suberyl chloride (D) | $C_{32}H_{42}N_2O_9$ | 598.7 | 599 |
| 10AFE | Leucine benzyl ester (A) | 4-nitrophenoxy-acetic acid (F) | methyl sebacoyl chloride (E) | $C_{34}H_{46}N_2O_9$ | 626.7 | 627 |
| 10BFA | Phenylalanine benzyl ester (B) | 4-nitrophenoxy-acetic acid (F) | glutaric anhydride (A) | $C_{31}H_{32}N_2O_9$ | 576.6 | 577 |
| 10BFB | Phenylalanine benzyl ester (B) | 4-nitrophenoxy-acetic acid (F) | heptanoyl chloride (B) | $C_{33}H_{38}N_2O_7$ | 574.7 | 575 |
| 10BFC | Phenylalanine benzyl ester (B) | 4-nitrophenoxy-acetic acid (F) | decanoic acid (C) | $C_{36}H_{44}N_2O_7$ | 616.8 | 617 |
| 10BFD | Phenylalanine benzyl ester (B) | 4-nitrophenoxy-acetic acid (F) | methyl suberyl chloride (D) | $C_{35}H_{40}N_2O_9$ | 632.7 | 633 |

TABLE 5-continued

REPRESENTATIVE COMPOUNDS (R₁ OF STRUCTURE (I) = BNO)

| Cpd. No. | First Component | Second Component | Third Component | Formula | MW Calcd | MW found (M − H) |
|---|---|---|---|---|---|---|
| 10BFE | Phenylalanine benzyl ester (B) | 4-nitrophenoxy-acetic acid (F) | methyl sebacoyl chloride (E) | $C_{37}H_{44}N_2O_9$ | 660.8 | 661 |
| 10AGA | Leucine benzyl ester (A) | 2-nitrocinnamic acid (G) | glutaric anhydride (A) | $C_{29}H_{34}N_2O_8$ | 538.6 | 539 |
| 10AGB | Leucine benzyl ester (A) | 2-nitrocinnamic acid (G) | heptanoyl chloride (B) | $C_{31}H_{40}N_2O_6$ | 536.7 | 537 |
| 10AGC | Leucine benzyl ester (A) | 2-nitrocinnamic acid (G) | decanoic acid (C) | $C_{34}H_{46}N_2O_6$ | 578.7 | 579 |
| 10AGD | Leucine benzyl ester (A) | 2-nitrocinnamic acid (G) | methyl suberyl chloride (D) | $C_{33}H_{42}N_2O_8$ | 594.7 | 595 |
| 10AGE | Leucine benzyl ester (A) | 2-nitrocinnamic acid (G) | methyl sebacoyl chloride (E) | $C_{35}H_{46}N_2O_8$ | 622.8 | 623 |
| 10BGA | Phenylalanine benzyl ester (B) | 2-nitrocinnamic acid (G) | glutaric anhydride (A) | $C_{25}H_{26}N_2O_8$ | 572.6 | 573 |
| 10BGB | Phenylalanine benzyl ester (B) | 2-nitrocinnamic acid (G) | heptanoyl chloride (B) | $C_{27}H_{32}N_2O_6$ | 570.3 | 571 |
| 10BGC | Phenylalanine benzyl ester (B) | 2-nitrocinnamic acid (G) | decanoic acid (C) | $C_{30}H_{38}N_2O_6$ | 612.8 | 613 |
| 10BGD | Phenylalanine benzyl ester (B) | 2-nitrocinnamic acid (G) | methyl suberyl chloride (D) | $C_{29}H_{34}N_2O_8$ | 628.7 | 629 |
| 10BGE | Phenylalanine benzyl ester (B) | 2-nitrocinnamic acid (G) | methyl sebacoyl chloride (E) | $C_{31}H_{38}N_2O_8$ | 656.8 | 657 |
| 10AHA | Leucine benzyl ester (A) | 3-nitrocinnamic acid (H) | glutaric anhydride (A) | $C_{29}H_{34}N_2O_8$ | 538.6 | 539 |
| 10AHB | Leucine benzyl ester (A) | 3-nitrocinnamic acid (H) | heptanoyl chloride (B) | $C_{31}H_{40}N_2O_6$ | 536.7 | 537 |
| 10AHC | Leucine benzyl ester (A) | 3-nitrocinnamic acid (H) | decanoic acid (C) | $C_{34}H_{46}N_2O_6$ | 578.7 | 579 |
| 10AHD | Leucine benzyl ester (A) | 3-nitrocinnamic acid (H) | methyl suberyl chloride (D) | $C_{33}H_{42}N_2O_8$ | 594.7 | 595 |
| 10AHE | Leucine benzyl ester (A) | 3-nitrocinnamic acid (H) | methyl sebacoyl chloride (E) | $C_{35}H_{46}N_2O_8$ | 622.8 | 623 |
| 10BHA | Phenylalanine benzyl ester (B) | 3-nitrocinnamic acid (H) | glutaric anhydride (A) | $C_{32}H_{32}N_2O_8$ | 572.6 | 573 |
| 10BHB | Phenylalanine benzyl ester (B) | 3-nitrocinnamic acid (H) | heptanoyl chloride (B) | $C_{34}H_{38}N_2O_6$ | 570.7 | 571 |
| 10BHC | Phenylalanine benzyl ester (B) | 3-nitrocinnamic acid (H) | decanoic acid (C) | $C_{37}H_{44}N_2O_6$ | 612.8 | 613 |
| 10BHD | Phenylalanine benzyl ester (B) | 3-nitrocinnamic acid (H) | methyl suberyl chloride (D) | $C_{36}H_{40}N_2O_8$ | 628.7 | 629 |
| 10BHE | Phenylalanine benzyl ester (B) | 3-nitrocinnamic acid (H) | methyl sebacoyl chloride (E) | $C_{38}H_{44}N_2O_8$ | 656.8 | 657 |
| 10AIA | Leucine benzyl ester (A) | 4-nitrocinnamic acid (I) | glutaric anhydride (A) | $C_{29}H_{34}N_2O_8$ | 538.6 | 539 |
| 10AIB | Leucine benzyl ester (A) | 4-nitrocinnamic acid (I) | heptanoyl chloride (B) | $C_{31}H_{40}N_2O_6$ | 536.7 | 537 |
| 10AIC | Leucine benzyl ester (A) | 4-nitrocinnamic acid (I) | decanoic acid (C) | $C_{34}H_{46}N_2O_6$ | 578.7 | 579 |

TABLE 5-continued

REPRESENTATIVE COMPOUNDS ($R_1$ OF STRUCTURE (I) = BNO)

| Cpd. No. | First Component | Second Component | Third Component | Formula | MW Calcd | MW found (M − H) |
|---|---|---|---|---|---|---|
| 10AID | Leucine benzyl ester (A) | 4-nitrocinnamic acid (I) | methyl suberyl chloride (D) | $C_{33}H_{42}N_2O_8$ | 594.7 | 595 |
| 10AIE | Leucine benzyl ester (A) | 4-nitrocinnamic acid (I) | methyl sebacoyl chloride (E) | $C_{35}H_{46}N_2O_8$ | 622.8 | 623 |
| 10BIA | Phenylalanine benzyl ester (B) | 4-nitrocinnamic acid (I) | glutaric anhydride (A) | $C_{32}H_{32}N_2O_8$ | 572.6 | 573 |
| 10BIB | Phenylalanine benzyl ester (B) | 4-nitrocinnamic acid (I) | heptanoyl chloride (B) | $C_{34}H_{38}N_2O_6$ | 570.7 | 571 |
| 10BIC | Phenylalanine benzyl ester (B) | 4-nitrocinnamic acid (I) | decanoic acid (C) | $C_{37}H_{44}N_2O_6$ | 612.8 | 613 |
| 10BID | Phenylalanine benzyl ester (B) | 4-nitrocinnamic acid (I) | methyl suberyl chloride (D) | $C_{36}H_{40}N_2O_8$ | 628.7 | 629 |
| 10BIE | Phenylalanine benzyl ester (B) | 4-nitrocinnamic acid (I) | methyl sebacoyl chloride (E) | $C_{38}H_{44}N_2O_8$ | 656.8 | 657 |
| 10AJA | Leucine benzyl ester (A) | 5-(2-nitrophenyl)-2-furoic acid (J) | glutaric anhydride (A) | $C_{31}H_{34}N_2O_9$ | 578.6 | 579 |
| 10AJB | Leucine benzyl ester (A) | 5-(2-nitrophenyl)-2-furoic acid (J) | heptanoyl chloride (B) | $C_{33}H_{40}N_2O_7$ | 576.7 | 577 |
| 10AJC | Leucine benzyl ester (A) | 5-(2-nitrophenyl)-2-furoic acid (J) | decanoic acid (C) | $C_{36}H_{46}N_2O_7$ | 618.8 | 619 |
| 10AJD | Leucine benzyl ester (A) | 5-(2-nitrophenyl)-2-furoic acid (J) | methyl suberyl chloride (D) | $C_{35}H_{42}N_2O_9$ | 634.7 | 635 |
| 10AJE | Leucine benzyl ester (A) | 5-(2-nitrophenyl)-2-furoic acid (J) | methyl sebacoyl chloride (E) | $C_{37}H_{46}N_2O_9$ | 662.8 | 663 |
| 10BJA | Phenylalanine benzyl ester (B) | 5-(2-nitrophenyl)-2-furoic acid (J) | glutaric anhydride (A) | $C_{34}H_{32}N_2O_9$ | 612.6 | 613 |
| 10BJB | Phenylalanine benzyl ester (B) | 5-(2-nitrophenyl)-2-furoic acid (J) | heptanoyl chloride (B) | $C_{36}H_{38}N_2O_7$ | 610.7 | 611 |
| 10BJC | Phenylalanine benzyl ester (B) | 5-(2-nitrophenyl)-2-furoic acid (J) | decanoic acid (C) | $C_{39}H_{44}N_2O_7$ | 652.8 | 653 |
| 10BJD | Phenylalanine benzyl ester (B) | 5-(2-nitrophenyl)-2-furoic acid (J) | methyl suberyl chloride (D) | $C_{38}H_{40}N_2O_9$ | 668.7 | 669 |
| 10BJE | Phenylalanine benzyl ester (B) | 5-(2-nitrophenyl)-2-furoic acid (J) | methyl sebacoyl chloride (E) | $C_{40}H_{44}N_2O_9$ | 696.8 | 697 |
| 10AKA | Leucine benzyl ester (A) | 5-(3-nitrophenyl)-2-furoic acid (K) | glutaric anhydride (A) | $C_{31}H_{34}N_2O_9$ | 578.6 | 579 |
| 10AKB | Leucine benzyl ester (A) | 5-(3-nitrophenyl)-2-furoic acid (K) | heptanoyl chloride (B) | $C_{33}H_{40}N_2O_7$ | 576.7 | 577 |
| 10AKC | Leucine benzyl ester (A) | 5-(3-nitrophenyl)-2-furoic acid (K) | decanoic acid (C) | $C_{36}H_{46}N_2O_7$ | 618.8 | 619 |

TABLE 5-continued

REPRESENTATIVE COMPOUNDS (R₁ OF STRUCTURE (I) = BNO)

| Cpd. No. | First Component | Second Component | Third Component | Formula | MW Calcd | MW found (M − H) |
|---|---|---|---|---|---|---|
| 10AKD | Leucine benzyl ester (A) | 5-(3-nitrophenyl)-2-furoic acid (K) | methyl suberyl chloride (D) | $C_{35}H_{42}N_2O_9$ | 634.7 | 635 |
| 10AKE | Leucine benzyl ester (A) | 5-(3-nitrophenyl)-2-furoic acid (K) | methyl sebacoyl chloride (E) | $C_{37}H_{46}N_2O_9$ | 662.8 | 663 |
| 10BKA | Phenylalanine benzyl ester (B) | 5-(3-nitrophenyl)-2-furoic acid (K) | glutaric anhydride (A) | $C_{34}H_{32}N_2O_9$ | 612.6 | 613 |
| 10BKB | Phenylalanine benzyl ester (B) | 5-(3-nitrophenyl)-2-furoic acid (K) | heptanoyl chloride (B) | $C_{36}H_{38}N_2O_7$ | 610.7 | 611 |
| 10BKC | Phenylalanine benzyl ester (B) | 5-(3-nitrophenyl)-2-furoic acid (K) | decanoic acid (C) | $C_{39}H_{44}N_2O_7$ | 652.8 | 653 |
| 10BKD | Phenylalanine benzyl ester (B) | 5-(3-nitrophenyl)-2-furoic acid (K) | methyl suberyl chloride (D) | $C_{38}H_{40}N_2O_9$ | 668.7 | 669 |
| 10BKE | Phenylalanine benzyl ester (B) | 5-(3-nitrophenyl)-2-furoic acid (K) | methyl sebacoyl chloride (E) | $C_{40}H_{44}N_2O_9$ | 696.8 | 697 |
| 10ALA | Leucine benzyl ester (A) | 5-(4-nitrophenyl)-2-furoic acid (L) | glutaric anhydride (A) | $C_{31}H_{34}N_2O_9$ | 578.6 | 579 |
| 10ALB | Leucine benzyl ester (A) | 5-(4-nitrophenyl)-2-furoic acid (L) | heptanoyl chloride (B) | $C_{33}H_{40}N_2O_7$ | 576.7 | 577 |
| 10ALC | Leucine benzyl ester (A) | 5-(4-nitrophenyl)-2-furoic acid (L) | decanoic acid (C) | $C_{36}H_{46}N_2O_7$ | 618.8 | 619 |
| 10ALD | Leucine benzyl ester (A) | 5-(4-nitrophenyl)-2-furoic acid (L) | methyl suberyl chloride (D) | $C_{35}H_{42}N_2O_9$ | 634.7 | 635 |
| 10ALE | Leucine benzyl ester (A) | 5-(4-nitrophenyl)-2-furoic acid (L) | methyl sebacoyl chloride (E) | $C_{37}H_{46}N_2O_9$ | 662.8 | 663 |
| 10BLA | Phenylalanine benzyl ester (B) | 5-(4-nitrophenyl)-2-furoic acid (L) | glutaric anhydride (A) | $C_{34}H_{32}N_2O_9$ | 612.6 | 613 |
| 10BLB | Phenylalanine benzyl ester (B) | 5-(4-nitrophenyl)-2-furoic acid (L) | heptanoyl chloride (B) | $C_{36}H_{38}N_2O_7$ | 610.7 | 611 |
| 10BLC | Phenylalanine benzyl ester (B) | 5-(4-nitrophenyl)-2-furoic acid (L) | decanoic acid (C) | $C_{39}H_{44}N_2O_7$ | 652.8 | 653 |
| 10BLD | Phenylalanine benzyl ester (B) | 5-(4-nitrophenyl)-2-furoic acid (L) | methyl suberyl chloride (D) | $C_{38}H_{40}N_2O_9$ | 668.7 | 669 |
| 10BLE | Phenylalanine benzyl ester (B) | 5-(4-nitrophenyl)-2-furoic acid (L) | methyl sebacoyl chloride (E) | $C_{40}H_{44}N_2O_9$ | 696.8 | 697 |

Example 6
Synthesis of Representative Compounds of Structure (I)

Using the same procedures as illustrated in Example 1, additional representative compounds were prepared using leucine benzyl ester (A) or phenylalanine benzyl ester (B) as the first component, and using various second components to illustrate embodiments wherein the "A" moiety of structure (I) is other than a direct bond. The corresponding compounds are listed below in Table 6.

TABLE 6

REPRESENTATIVE COMPOUNDS ($R_1$ OF STRUCTURE (I) = OH)

| Cpd. No. | First Component | Second Component | Third Component | Formula | MW Calcd | MW found (M − H) |
|---|---|---|---|---|---|---|
| 11AAA | Leucine benzyl ester (A) | 2-nitrophenyl-acetic acid (A) | glutaric anhydride (A) | $C_{21}H_{28}N_2O_8$ | 436.5 | 437 |
| 11AAB | Leucine benzyl ester (A) | 2-nitrophenyl-acetic acid (A) | heptanoyl chloride (B) | $C_{23}H_{34}N_2O_6$ | 434.5 | 435 |
| 11AAC | Leucine benzyl ester (A) | 2-nitrophenyl-acetic acid (A) | decanoic acid (C) | $C_{26}H_{40}N_2O_6$ | 476.6 | 477 |
| 11AAD | Leucine benzyl ester (A) | 2-nitrophenyl-acetic acid (A) | methyl suberyl chloride (D) | $C_{25}H_{36}N_2O_8$ | 492.6 | 493 |
| 11AAE | Leucine benzyl ester (A) | 2-nitrophenyl-acetic acid (A) | methyl sebacoyl chloride (E) | $C_{27}H_{40}N_2O_8$ | 520.6 | 521 |
| 11BAA | Phenylalanine benzyl ester (B) | 2-nitrophenyl-acetic acid (A) | glutaric anhydride (A) | $C_{24}H_{26}N_2O_8$ | 470.5 | 471 |
| 11BAB | Phenylalanine benzyl ester (B) | 2-nitrophenyl-acetic acid (A) | heptanoyl chloride (B) | $C_{26}H_{32}N_2O_6$ | 468.5 | 469 |
| 11BAC | Phenylalanine benzyl ester (B) | 2-nitrophenyl-acetic acid (A) | decanoic acid (C) | $C_{29}H_{38}N_2O_6$ | 510.6 | 511 |
| 11BAD | Phenylalanine benzyl ester (B) | 2-nitrophenyl-acetic acid (A) | methyl suberyl chloride (D) | $C_{28}H_{34}N_2O_8$ | 526.6 | 527 |
| 11BAE | Phenylalanine benzyl ester (B) | 2-nitrophenyl-acetic acid (A) | methyl sebacoyl chloride (E) | $C_{30}H_{38}N_2O_8$ | 554.6 | 555 |
| 11ABA | Leucine benzyl ester (A) | 3-nitrophenyl-acetic acid (B) | glutaric anhydride (A) | $C_{21}H_{28}N_2O_8$ | 436.5 | 437 |
| 11ABB | Leucine benzyl ester (A) | 3-nitrophenyl-acetic acid (B) | heptanoyl chloride (B) | $C_{23}H_{34}N_2O_6$ | 434.5 | 435 |
| 11ABC | Leucine benzyl ester (A) | 3-nitrophenyl-acetic acid (B) | decanoic acid (C) | $C_{26}H_{40}N_2O_6$ | 476.6 | 477 |
| 11ABD | Leucine benzyl ester (A) | 3-nitrophenyl-acetic acid (B) | methyl suberyl chloride (D) | $C_{25}H_{36}N_2O_8$ | 492.6 | 493 |
| 11ABE | Leucine benzyl ester (A) | 3-nitrophenyl-acetic acid (B) | methyl sebacoyl chloride (E) | $C_{27}H_{40}N_2O_8$ | 520.6 | 521 |
| 11BBA | Phenylalanine benzyl ester (B) | 3-nitrophenyl-acetic acid (B) | glutaric anhydride (A) | $C_{24}H_{26}N_2O_8$ | 470.5 | 471 |
| 11BBB | Phenylalanine benzyl ester (B) | 3-nitrophenyl-acetic acid (B) | heptanoyl chloride (B) | $C_{26}H_{32}N_2O_6$ | 468.5 | 469 |
| 11BBC | Phenylalanine benzyl ester (B) | 3-nitrophenyl-acetic acid (B) | decanoic acid (C) | $C_{29}H_{38}N_2O_6$ | 510.6 | 511 |
| 11BBD | Phenylalanine benzyl ester (B) | 3-nitrophenyl-acetic acid (B) | methyl suberyl chloride (D) | $C_{28}H_{34}N_2O_8$ | 526.6 | 527 |
| 11BBE | Phenylalanine benzyl ester (B) | 3-nitrophenyl-acetic acid (B) | methyl sebacoyl chloride (E) | $C_{30}H_{38}N_2O_8$ | 554.6 | 555 |
| 11ACA | Leucine benzyl ester (A) | 4-nitrophenyl-acetic acid (C) | glutaric anhydride (A) | $C_{21}H_{28}N_2O_8$ | 436.5 | 437 |

TABLE 6-continued

REPRESENTATIVE COMPOUNDS ($R_1$ OF STRUCTURE (I) = OH)

| Cpd. No. | First Component | Second Component | Third Component | Formula | MW Calcd | MW found (M − H) |
|---|---|---|---|---|---|---|
| 11ACB | Leucine benzyl ester (A) | 4-nitrophenyl-acetic acid (C) | heptanoyl chloride (B) | $C_{23}H_{34}N_2O_6$ | 434.5 | 435 |
| 11ACC | Leucine benzyl ester (A) | 4-nitrophenyl-acetic acid (C) | decanoic acid (C) | $C_{26}H_{40}N_2O_6$ | 476.6 | 477 |
| 11ACD | Leucine benzyl ester (A) | 4-nitrophenyl-acetic acid (C) | methyl suberyl chloride (D) | $C_{25}H_{36}N_2O_8$ | 492.6 | 493 |
| 11ACE | Leucine benzyl ester (A) | 4-nitrophenyl-acetic acid (C) | methyl sebacoyl chloride (E) | $C_{27}H_{40}N_2O_8$ | 520.6 | 521 |
| 11BCA | Phenylalanine benzyl ester (B) | 4-nitrophenyl-acetic acid (C) | glutaric anhydride (A) | $C_{24}H_{26}N_2O_8$ | 470.5 | 471 |
| 11BCB | Phenylalanine benzyl ester (B) | 4-nitrophenyl-acetic acid (C) | heptanoyl chloride (B) | $C_{26}H_{32}N_2O_6$ | 468.5 | 469 |
| 11BCC | Phenylalanine benzyl ester (B) | 4-nitrophenyl-acetic acid (C) | decanoic acid (C) | $C_{29}H_{38}N_2O_6$ | 510.6 | 511 |
| 11BCD | Phenylalanine benzyl ester (B) | 4-nitrophenyl-acetic acid (C) | methyl suberyl chloride (D) | $C_{28}H_{34}N_2O_8$ | 526.6 | 527 |
| 11BCE | Phenylalanine benzyl ester (B) | 4-nitrophenyl-acetic acid (C) | methyl sebacoyl chloride (E) | $C_{30}H_{38}N_2O_8$ | 554.6 | 555 |
| 11ADA | Leucine benzyl ester (A) | 2-nitrophenoxy-acetic acid (D) | glutaric anhydride (A) | $C_{21}H_{28}N_2O_9$ | 452.5 | 453 |
| 11ADB | Leucine benzyl ester (A) | 2-nitrophenoxy-acetic acid (D) | heptanoyl chloride (B) | $C_{23}H_{34}N_2O_7$ | 450.5 | 451 |
| 11ADC | Leucine benzyl ester (A) | 2-nitrophenoxy-acetic acid (D) | decanoic acid (C) | $C_{26}H_{40}N_2O_7$ | 492.6 | 493 |
| 11ADD | Leucine benzyl ester (A) | 2-nitrophenoxy-acetic acid (D) | methyl suberyl chloride (D) | $C_{25}H_{36}N_2O_9$ | 508.6 | 509 |
| 11ADE | Leucine benzyl ester (A) | 2-nitrophenoxy-acetic acid (D) | methyl sebacoyl chloride (E) | $C_{27}H_{40}N_2O_9$ | 536.6 | 537 |
| 11BDA | Phenylalanine benzyl ester (B) | 2-nitrophenoxy-acetic acid (D) | glutaric anhydride (A) | $C_{24}H_{26}N_2O_9$ | 486.5 | 487 |
| 11BDB | Phenylalanine benzyl ester (B) | 2-nitrophenoxy-acetic acid (D) | heptanoyl chloride (B) | $C_{26}H_{32}N_2O_7$ | 484.5 | 485 |
| 11BDC | Phenylalanine benzyl ester (B) | 2-nitrophenoxy-acetic acid (D) | decanoic acid (C) | $C_{29}H_{38}N_2O_7$ | 526.6 | 527 |
| 11BDD | Phenylalanine benzyl ester (B) | 2-nitrophenoxy-acetic acid (D) | methyl suberyl chloride (D) | $C_{28}H_{34}N_2O_9$ | 542.6 | 543 |
| 11BDE | Phenylalanine benzyl ester (B) | 2-nitrophenoxy-acetic acid (D) | methyl sebacoyl chloride (E) | $C_{30}H_{38}N_2O_9$ | 570.6 | 571 |
| 11AEA | Leucine benzyl ester (A) | 3-nitrophenoxy-acetic acid (E) | glutaric anhydride (A) | $C_{21}H_{28}N_2O_9$ | 452.5 | 453 |
| 11AEB | Leucine benzyl ester (A) | 3-nitrophenoxy-acetic acid (E) | heptanoyl chloride (B) | $C_{23}H_{34}N_2O_7$ | 450.5 | 451 |
| 11AEC | Leucine benzyl ester (A) | 3-nitrophenoxy-acetic acid (E) | decanoic acid (C) | $C_{26}H_{40}N_2O_7$ | 492.6 | 493 |
| 11AED | Leucine benzyl ester (A) | 3-nitrophenoxy-acetic acid (E) | methyl suberyl chloride (D) | $C_{25}H_{36}N_2O_9$ | 508.6 | 509 |
| 11AEE | Leucine benzyl ester (A) | 3-nitrophenoxy-acetic acid (E) | methyl sebacoyl chloride (E) | $C_{27}H_{40}N_2O_9$ | 536.6 | 537 |

TABLE 6-continued

REPRESENTATIVE COMPOUNDS ($R_1$ OF STRUCTURE (I) = OH)

| Cpd. No. | First Component | Second Component | Third Component | Formula | MW Calcd | MW found (M − H) |
|---|---|---|---|---|---|---|
| 11BEA | Phenylalanine benzyl ester (B) | 3-nitrophenoxy-acetic acid (E) | glutaric anhydride (A) | $C_{24}H_{26}N_2O_9$ | 486.5 | 487 |
| 11BEB | Phenylalanine benzyl ester (B) | 3-nitrophenoxy-acetic acid (E) | heptanoyl chloride (B) | $C_{26}H_{32}N_2O_7$ | 484.5 | 485 |
| 11BEC | Phenylalanine benzyl ester (B) | 3-nitrophenoxy-acetic acid (E) | decanoic acid (C) | $C_{29}H_{38}N_2O_7$ | 526.6 | 527 |
| 11BED | Phenylalanine benzyl ester (B) | 3-nitrophenoxy-acetic acid (E) | methyl suberyl chloride (D) | $C_{28}H_{34}N_2O_9$ | 542.6 | 543 |
| 11BEE | Phenylalanine benzyl ester (B) | 3-nitrophenoxy-acetic acid (E) | methyl sebacoyl chloride (E) | $C_{30}H_{38}N_2O_9$ | 570.6 | 571 |
| 11AFA | Leucine benzyl ester (A) | 4-nitrophenoxy-acetic acid (F) | glutaric anhydride (A) | $C_{21}H_{28}N_2O_9$ | 452.5 | 453 |
| 11AFB | Leucine benzyl ester (A) | 4-nitrophenoxy-acetic acid (F) | heptanoyl chloride (B) | $C_{23}H_{34}N_2O_7$ | 450.5 | 451 |
| 11AFC | Leucine benzyl ester (A) | 4-nitrophenoxy-acetic acid (F) | decanoic acid (C) | $C_{26}H_{40}N_2O_7$ | 492.6 | 493 |
| 11AFD | Leucine benzyl ester (A) | 4-nitrophenoxy-acetic acid (F) | methyl suberyl chloride (D) | $C_{25}H_{36}N_2O_9$ | 508.6 | 509 |
| 11AFE | Leucine benzyl ester (A) | 4-nitrophenoxy-acetic acid (F) | methyl sebacoyl chloride (E) | $C_{27}H_{40}N_2O_9$ | 536.6 | 537 |
| 11BFA | Phenylalanine benzyl ester (B) | 4-nitrophenoxy-acetic acid (F) | glutaric anhydride (A) | $C_{24}H_{26}N_2O_9$ | 486.5 | 487 |
| 11BFB | Phenylalanine benzyl ester (B) | 4-nitrophenoxy-acetic acid (F) | heptanoyl chloride (B) | $C_{26}H_{32}N_2O_7$ | 484.5 | 485 |
| 11BFC | Phenylalanine benzyl ester (B) | 4-nitrophenoxy acetic acid (F) | decanoic acid (C) | $C_{29}H_{38}N_2O_7$ | 526.6 | 527 |
| 11BFD | Phenylalanine benzyl ester (B) | 4-nitrophenoxy-acetic acid (F) | methyl suberyl chloride (D) | $C_{28}H_{34}N_2O_9$ | 542.6 | 543 |
| 11BFE | Phenylalanine benzyl ester (B) | 4-nitrophenoxy-acetic acid (F) | methyl sebacoyl chloride (E) | $C_{30}H_{38}N_2O_9$ | 570.6 | 571 |
| 11AGA | Leucine benzyl ester (A) | 2-nitrocinnamic acid (G) | glutaric anhydride (A) | $C_{22}H_{28}N_2O_8$ | 448.5 | 449 |
| 11AGB | Leucine benzyl ester (A) | 2-nitrocinnamic acid (G) | heptanoyl chloride (B) | $C_{24}H_{34}N_2O_6$ | 446.5 | 447 |
| 11AGC | Leucine benzyl ester (A) | 2-nitrocinnamic acid (G) | decanoic acid (C) | $C_{27}H_{40}N_2O_6$ | 488.6 | 489 |
| 11AGD | Leucine benzyl ester (A) | 2-nitrocinnamic acid (G) | methyl suberyl chloride (D) | $C_{26}H_{36}N_2O_8$ | 504.6 | 505 |
| 11AGE | Leucine benzyl ester (A) | 2-nitrocinnamic acid (G) | methyl sebacoyl chloride (E) | $C_{28}H_{40}N_2O_8$ | 532.6 | 533 |
| 11BGA | Phenylalanine benzyl ester (B) | 2-nitrocinnamic acid (G) | glutaric anhydride (A) | $C_{25}H_{26}N_2O_8$ | 482.5 | 483 |
| 11BGB | Phenylalanine benzyl ester (B) | 2-nitrocinnamic acid (G) | heptanoyl chloride (B) | $C_{27}H_{32}N_2O_6$ | 480.6 | 481 |
| 11BGC | Phenylalanine benzyl ester (B) | 2-nitrocinnamic acid (G) | decanoic acid (C) | $C_{30}H_{38}N_2O_6$ | 522.6 | 523 |
| 11BGD | Phenylalanine benzyl ester (B) | 2-nitrocinnamic acid (G) | methyl suberyl chloride (D) | $C_{29}H_{34}N_2O_8$ | 538.6 | 539 |

TABLE 6-continued

REPRESENTATIVE COMPOUNDS ($R_1$ OF STRUCTURE (I) = OH)

| Cpd. No. | First Component | Second Component | Third Component | Formula | MW Calcd | MW found (M − H) |
|---|---|---|---|---|---|---|
| 11BGE | Phenylalanine benzyl ester (B) | 2-nitrocinnamic acid (G) | methyl sebacoyl chloride (E) | $C_{31}H_{38}N_2O_8$ | 566.6 | 567 |
| 11AHA | Leucine benzyl ester (A) | 3-nitrocinnamic acid (H) | glutaric anhydride (A) | $C_{22}H_{28}N_2O_8$ | 448.5 | 449 |
| 11AHB | Leucine benzyl ester (A) | 3-nitrocinnamic acid (H) | heptanoyl chloride (B) | $C_{24}H_{34}N_2O_6$ | 446.5 | 447 |
| 11AHC | Leucine benzyl ester (A) | 3-nitrocinnamic acid (H) | decanoic acid (C) | $C_{27}H_{40}N_2O_6$ | 488.6 | 489 |
| 11AHD | Leucine benzyl ester (A) | 3-nitrocinnamic acid (H) | methyl suberyl chloride (D) | $C_{26}H_{36}N_2O_8$ | 504.6 | 505 |
| 11AHE | Leucine benzyl ester (A) | 3-nitrocinnamic acid (H) | methyl sebacoyl chloride (E) | $C_{28}H_{40}N_2O_8$ | 532.6 | 533 |
| 11BHA | Phenylalanine benzyl ester (B) | 3-nitrocinnamic acid (H) | glutaric anhydride (A) | $C_{25}H_{26}N_2O_8$ | 482.5 | 483 |
| 11BHB | Phenylalanine benzyl ester (B) | 3-nitrocinnamic acid (H) | heptanoyl chloride (B) | $C_{27}H_{32}N_2O_6$ | 480.6 | 481 |
| 11BHC | Phenylalanine benzyl ester (B) | 3-nitrocinnamic acid (H) | decanoic acid (C) | $C_{30}H_{38}N_2O_6$ | 522.6 | 523 |
| 11BHD | Phenylalanine benzyl ester (B) | 3-nitrocinnamic acid (H) | methyl suberyl chloride (D) | $C_{29}H_{34}N_2O_8$ | 538.6 | 539 |
| 11BHE | Phenylalanine benzyl ester (B) | 3-nitrocinnamic acid (H) | methyl sebacoyl chloride (E) | $C_{31}H_{38}N_2O_8$ | 566.6 | 567 |
| 11AIA | Leucine benzyl ester (A) | 4-nitrocinnamic acid (I) | glutaric anhydride (A) | $C_{22}H_{28}N_2O_8$ | 448.5 | 449 |
| 11AIB | Leucine benzyl ester (A) | 4-nitrocinnamic acid (I) | heptanoyl chloride (B) | $C_{24}H_{34}N_2O_6$ | 446.5 | 447 |
| 11AIC | Leucine benzyl ester (A) | 4-nitrocinnamic acid (I) | decanoic acid (C) | $C_{27}H_{40}N_2O_6$ | 488.6 | 489 |
| 11AID | Leucine benzyl ester (A) | 4-nitrocinnamic acid (I) | methyl suberyl chloride (D) | $C_{26}H_{36}N_2O_8$ | 504.6 | 505 |
| 11AIE | Leucine benzyl ester (A) | 4-nitrocinnamic acid (I) | methyl sebacoyl chloride (E) | $C_{28}H_{40}N_2O_8$ | 532.6 | 533 |
| 11BIA | Phenylalanine benzyl ester (B) | 4-nitrocinnamic acid (I) | glutaric anhydride (A) | $C_{25}H_{26}N_2O_8$ | 482.5 | 483 |
| 11BIB | Phenylalanine benzyl ester (B) | 4-nitrocinnamic acid (I) | heptanoyl chloride (B) | $C_{27}H_{32}N_2O_6$ | 480.6 | 481 |
| 11BIC | Phenylalanine benzyl ester (B) | 4-nitrocinnamic acid (I) | decanoic acid (C) | $C_{30}H_{38}N_2O_6$ | 522.6 | 523 |
| 11BID | Phenylalanine benzyl ester (B) | 4-nitrocinnamic acid (I) | methyl suberyl chloride (D) | $C_{29}H_{34}N_2O_8$ | 538.6 | 539 |
| 11BIE | Phenylalanine benzyl ester (B) | 4-nitrocinnamic acid (I) | methyl sebacoyl chloride (E) | $C_{31}H_{38}N_2O_8$ | 566.6 | 567 |
| 11AJA | Leucine benzyl ester (A) | 5-(2-nitrophenyl)-2-furoic acid (J) | glutaric anhydride (A) | $C_{24}H_{28}N_2O_9$ | 488.5 | 489 |
| 11AJB | Leucine benzyl ester (A) | 5-(2-nitrophenyl)-2-furoic acid (J) | heptanoyl chloride (B) | $C_{26}H_{34}N_2O_7$ | 486.6 | 487 |
| 11AJC | Leucine benzyl ester (A) | 5-(2-nitrophenyl)-2-furoic acid (J) | decanoic acid (C) | $C_{29}H_{40}N_2O_7$ | 528.6 | 529 |

TABLE 6-continued

REPRESENTATIVE COMPOUNDS ($R_1$ OF STRUCTURE (I) = OH)

| Cpd. No. | First Component | Second Component | Third Component | Formula | MW Calcd | MW found (M − H) |
|---|---|---|---|---|---|---|
| 11AJD | Leucine benzyl ester (A) | 5-(2-nitrophenyl)-2-furoic acid (J) | methyl suberyl chloride (D) | $C_{28}H_{36}N_2O_9$ | 544.6 | 545 |
| 11AJE | Leucine benzyl ester (A) | 5-(2-nitrophenyl)-2-furoic acid (J) | methyl sebacoyl chloride (E) | $C_{30}H_{40}N_2O_9$ | 572.7 | 573 |
| 11BJA | Phenylalanine benzyl ester (B) | 5-(2-nitrophenyl)-2-furoic acid (J) | glutaric anhydride (A) | $C_{27}H_{26}N_2O_9$ | 522.5 | 523 |
| 11BJB | Phenylalanine benzyl ester (B) | 5-(2-nitrophenyl)-2-furoic acid (J) | heptanoyl chloride (B) | $C_{29}H_{32}N_2O_7$ | 520.6 | 521 |
| 11BJC | Phenylalanine benzyl ester (B) | 5-(2-nitrophenyl)-2-furoic acid (J) | decanoic acid (C) | $C_{32}H_{38}N_2O_7$ | 562.7 | 563 |
| 11BJD | Phenylalanine benzyl ester (B) | 5-(2-nitrophenyl)-2-furoic acid (J) | methyl suberyl chloride (D) | $C_{31}H_{34}N_2O_9$ | 578.6 | 579 |
| 11BJE | Phenylalanine benzyl ester (B) | 5-(2-nitrophenyl)-2-furoic acid (J) | methyl sebacoyl chloride (E) | $C_{33}H_{38}N_2O_9$ | 606.7 | 607 |
| 11AKA | Leucine benzyl ester (A) | 5-(3-nitrophenyl)-2-furoic acid (K) | glutaric anhydride (A) | $C_{24}H_{28}N_2O_9$ | 488.5 | 489 |
| 11AKB | Leucine benzyl ester (A) | 5-(3-nitrophenyl)-2-furoic acid (K) | heptanoyl chloride (B) | $C_{26}H_{34}N_2O_7$ | 486.6 | 487 |
| 11AKC | Leucine benzyl ester (A) | 5-(3-nitrophenyl)-2-furoic acid (K) | decanoic acid (C) | $C_{29}H_{40}N_2O_7$ | 528.6 | 529 |
| 11AKD | Leucine benzyl ester (A) | 5-(3-nitrophenyl)-2-furoic acid (K) | methyl suberyl chloride (D) | $C_{28}H_{36}N_2O_9$ | 544.6 | 545 |
| 11AKE | Leucine benzyl ester (A) | 5-(3-nitrophenyl)-2-furoic acid (K) | methyl sebacoyl chloride (E) | $C_{30}H_{40}N_2O_9$ | 572.7 | 573 |
| 11BKA | Phenylalanine benzyl ester (B) | 5-(3-nitrophenyl)-2-furoic acid (K) | glutaric anhydride (A) | $C_{27}H_{26}N_2O_9$ | 522.5 | 523 |
| 11BKB | Phenylalanine benzyl ester (B) | 5-(3-nitrophenyl)-2-furoic acid (K) | heptanoyl chloride (B) | $C_{29}H_{32}N_2O_7$ | 520.6 | 521 |
| 11BKC | Phenylalanine benzyl ester (B) | 5-(3-nitrophenyl)-2-furoic acid (K) | decanoic acid (C) | $C_{32}H_{38}N_2O_7$ | 562.7 | 563 |
| 11BKD | Phenylalanine benzyl ester (B) | 5-(3-nitrophenyl)-2-furoic acid (K) | methyl suberyl chloride (D) | $C_{31}H_{34}N_2O_9$ | 578.6 | 579 |
| 11BKE | Phenylalanine benzyl ester (B) | 5-(3-nitrophenyl)-2-furoic acid (K) | methyl sebacoyl chloride (E) | $C_{33}H_{38}N_2O_9$ | 606.7 | 607 |
| 11ALA | Leucine benzyl ester (A) | 5-(4-nitrophenyl)-2-furoic acid (L) | glutaric anhydride (A) | $C_{24}H_{28}N_2O_9$ | 488.5 | 489 |
| 11ALB | Leucine benzyl ester (A) | 5-(4-nitrophenyl)-2-furoic acid (L) | heptanoyl chloride (B) | $C_{26}H_{34}N_2O_7$ | 486.6 | 487 |
| 11ALC | Leucine benzyl ester (A) | 5-(4-nitrophenyl)-2-furoic acid (L) | decanoic acid (C) | $C_{29}H_{40}N_2O_7$ | 528.6 | 529 |
| 11ALD | Leucine benzyl ester (A) | 5-(4-nitrophenyl)-2-furoic acid (L) | methyl suberyl chloride (D) | $C_{28}H_{36}N_2O_9$ | 544.6 | 545 |
| 11ALE | Leucine benzyl ester (A) | 5-(4-nitrophenyl)-2-furoic acid (L) | methyl sebacoyl chloride (E) | $C_{30}H_{40}N_2O_9$ | 572.7 | 573 |
| 11BLA | Phenylalanine benzyl ester (B) | 5-(4-nitrophenyl)-2-furoic acid (L) | glutaric anhydride (A) | $C_{27}H_{26}N_2O_9$ | 522.5 | 523 |
| 11BLB | Phenylalanine benzyl ester (B) | 5-(4-nitrophenyl)-2-furoic acid (L) | heptanoyl chloride (B) | $C_{29}H_{32}N_2O_7$ | 520.6 | 521 |

TABLE 6-continued

REPRESENTATIVE COMPOUNDS ($R_1$ OF STRUCTURE (I) = OH)

| Cpd. No. | First Component | Second Component | Third Component | Formula | MW Calcd | MW found (M – H) |
|---|---|---|---|---|---|---|
| 11BLC | Phenylalanine benzyl ester (B) | 5-(4-nitrophenyl)-2-furoic acid (L) | decanoic acid (C) | $C_{32}H_{38}N_2O_7$ | 562.7 | 563 |
| 11BLD | Phenylalanine benzyl ester (B) | 5-(4-nitrophenyl)-2-furoic acid (L) | methyl suberyl chloride (D) | $C_{31}H_{34}N_2O_9$ | 578.6 | 579 |
| 11BLE | Phenylalanine benzyl ester (B) | 5-(4-nitrophenyl)-2-furoic acid (L) | methyl sebacoyl chloride (E) | $C_{26}H_{32}N_2O_9$ | 606.7 | 607 |

Example 7

Biological Activity

Neuronal Viability Assay

This assay is used to assess the ability of compounds of this invention to protect neurons from glutamate-induced excitotoxic cell death. Primary cell culture is performed with embryonic day 18 rat hippocampal and cortical neurons that are plated into Biocoat Poly-D-Lysine precoated 96-well plates (Becton-Dickinson, Bedford, Mass.; catalog no. 356461) at a density of 21,000 cells/well. The cells are grown in Neurobasal media (Gibco/Life Technologies, Rockville, Md., catalog no. 21103049) supplemented with B27, penicillin (100 IU/ml), streptomycin (100 µg/ml) and 500 µM L-glutamine. This media supports growth of pure neuronal cultures as contaminating glial cells that may be initially present do not survive in the media conditions. At 17 days after culture, media is aspirated from wells and 100 µl solution of test compound in assay buffer (HBSS supplemented with 25 mM HEPES) is added. After 10 min of incubation, 100 µL of test compound solution in assay buffer supplemented with 200 µM glutamate/20 µM glycine is added. Ten min later, cells are treated with 100 µl of a 20 µM solution of MK-801 (an NMDA receptor antagonist that blocks $Ca^{2+}$ influx; Sigma-Aldrich, St. Louis, Mo., catalog no. M-107) in Neurobasal media. After 24 hrs, the extent of cell death is quantitated by measuring lactate dehydrogenase activity released by lysed cells using a calorimetric Cytotoxicity Detection Kit (Roche Diagnostics GmbH, Mannheim, Germany, catalog no. 1 644 793) and following the manufacturer's instructions.

In this assay, preferred compounds have a mean neuronal viability of 0.6 or less. To this end, preferred compounds of this invention include the following: 6AAD, 6AAE, 6ABE, 6ABF, 6ACE, 6BAA, 6BAE, 6BAG, 6BCA, 6BCB, 6CCA, 7AAC, 7AAE, 7ABA, 7BAA, 7BBD, 9AAA, 9AAB, 9AAE, 9ABA, 9ABB, 9ABC, 9BAD, 9BAE, 9BBA, 9BBD, 9CAA, 9CAB, 9CAC, 9CAD, 9CBA, 9CBC, 9CBD, 9CBE, 9DBA, 9DBB, 9DBC, 8AAB, 8AAE, 8ABB, 8ABE, 8BAB, 8BBA, 8BBB, 8CAB, 8CAD and 8CBA.

Displacement Assays of an Adenine Nucleotide Translocase (ANT) Ligand from Isolated Mitochondria using Test Compounds Compound 1 below is a $^{125}I$-labeled atractyloside derivative that binds to the mitochondrial adenine nucleotide translocase with high affinity ($IC_{50}$=300 nM in a displacement assay using [$^3H$]-ADP as ligand). Thus, Compound 1 may be used as the radioligand to measure efficacy of binding of the compounds of this invention.

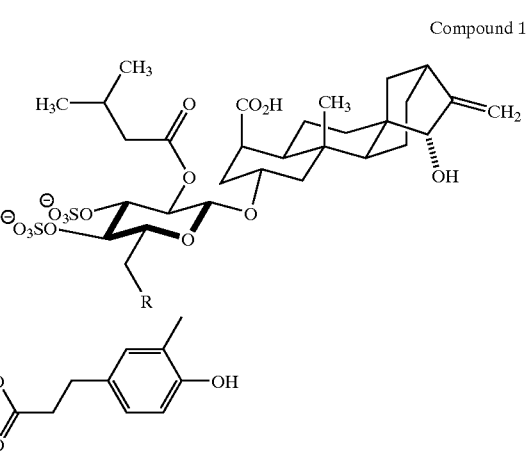

Compound 1

Competition binding assays are performed using bovine cardiac mitochondria. One microgram aliquots of mitochondrial protein are incubated with 100 µl binding buffer (10 mM Tris, 120 mM KCl, 6 mM $MgCl_2$, 1 mM EDTA, pH 7.4) containing 0.5 nM Compound 1 and a test compound at various concentrations (10 or 100 µM). Mixtures are incubated for one hour on ice, at the end of which unbound ligand is separated by centrifugation. Supernatants containing unbound Compound 1 are aspirated and discarded. Mitochondrial pellets are washed with four volumes of cold binding buffer and counted in a Micromedic 4/200 automatic gamma counter. For higher throughput, assays are performed in a 96 well microtitre well format. Unbound ligand is removed by filtration and washes through glass fiber filter mats (Whatman GF/B paper, catalog no. FPXLR-196, Brandel, Inc., Gaithersburg, Md.). The radioactivity associated with the mitochondrial pellets retained in the filter mat is determined in a 1450 Wallac MicroBeta TriLux liquid scintillation and luminescence counter (EG&G Wallac, Gaithersburg, Md.). In this assay, preferred compounds of this invention (at 10 µM) displace the radioligand (i.e., Compound 1) such that 80% or less of the radioactivity of the mitochondrial pellets is detected. To this end, preferred compounds are 6AAB, 6AAD, 6ABA, 6ABB, 6ABD, 6ACB, 6ACC, 6BAB, 6BAC, 6BAD, 6BBA, 6BCB, 6BCF, 6CAB, 6CAC, 6CAD, 6CAG, 6CBB, 6CBD, 6CBE, 6CCC, 6CCD, 7AAE, 8AAE, 8BBC and 8CBC.

Example 8

Chondrocyte Cytoprotection

This example illustrates the ability of a test compound, 9DBC, to mediate chondrocyte cytoprotection. More specifically, the test compound was found to protect against (1) trigger-induced cell death (i.e., viability), (2) trigger-induced inhibition of collagen synthesis, (3) trigger-induced GAG release, and (4) IL-1-mediated GAG release and NO generation. The procedures employed are set forth below, while the results of these assays are summarized in Table 7.

tetrazolium saletin to a red formazan product. The results were expressed as the percent of cells dead as to the release of LDH by the control cells.

Gylcosaminoglycans (GAG) Release Assay

The enhanced release from chondrocytes of glycosaminoglycans (GAG) is a central feature of osteoarthritic

TABLE 7

SUMMARY OF RESULTS

| | Viability[1] (cells) | | Collagen[2] (cells) | | | GAG[3] (cells) | | | GAG[4] (Slices) NO[4] (Slices) | |
|---|---|---|---|---|---|---|---|---|---|---|
| Trigger | NOC-12 | SIN-1 | NOC-12 | SIN-1 | IL-1 | NOC-12 | SIN-1 | IL-1 | IL-1 | IL-1 |
| ~$EC_{50}$ | 1 nm | 1 nm | 1 $\mu$m | >1 $\mu$m | >1 $\mu$m | 100 nm | 100 nm | 100 nm | 10 $\mu$m | 10 $\mu$m |

[1]Protection against trigger-induced cell death. TC 28 cells as monolayer culture Trigger: NOC-12, 250 $\mu$M, SIN-1, 100 $\mu$M.
[2]Protection against trigger-induced inhibition of collagen synthesis. TC 28 cells cultured in polyHEME plates .trigger NOC-12, 25 $\mu$M; SIN-1, 10 $\mu$m
[3]Protection against trigger-induced GAG release. TC 28 cells cultured in polyHEME plates .trigger NOC-12, 25 $\mu$M; SIN-1, 10 $\mu$M, IL-1. 10 ng/ml
[4]Protection against IL-1-mediated GAG release and NO generation in bovine cartilage slices. IL-1 trigger, 10 ng/ml.

Chondrocyte Function Screening Assays

Cell culture: Chondrocytic TC28 cells were maintained in monolayer culture in DMEM/Ham's F12 (1:1) and supplemented with 10% FCS, 1% L-glutamine, 100 units/ml Penicillin and 50 mg/ml Streptomycin (Omega Scientific, Tarzana, Calif.) and cultured at 37$f$C with 5% $CO_2$. Additionally, to further study chondrocytic cells in a more physiologic nonadherent state, in some experiments, TC28 cells were transferred to 6 well plates that had been previously coated for 18 hours at 22° C. with 10% (v/v) in 95% ethanol solution of the cell adhesion inhibitor poly 2-Hydroxyethyl methacrylate (polyHEME), followed by two washes in PBS. Complete DMEM/Ham's F12 medium was then added to the wells and the cells studied for up to 72 hours in culture. Type II collagen and aggrecan expression were confirmed using RT-PCR, which verified maintenance of chondrocyte phenotype.

Screening Assays: Compound 9DBC was screened for chondrocyte protective effects in vitro. The agonists employed have included a donor of nitric oxide (NOC-12, 250 uM), a donor of peroxynitrite (SIN-1, 100 uM), and human recombinant IL-1 beta (10 ng/ml). Cytotoxicity was measured via standard lactate dehydrogenase (LDH) release assay as described below. Collagen synthesis was monitored by 3H proline incorporation into TC28 cells, TCA precipitation of proteins, followed by assay of radioactivity in collagenae sensitive proteibn as outlined in Johnson et al (*Arthritis Rheum.* 43:1560–70, 2000). NO was detected by using the Greiss reaction.

Cytotoxicity Assay $10^5$ TC28 cells (DMEM/F12 media with 10% FCS, 1% glutamine, 1% P/S) were plated each well in a 96 well plate and allowed to adhere overnight. The cells were washed once with PBS and media changed to contain only 1% FCS. Compound 9DBC at various concentrations was added to the cells for a pretreatment of 1 hr. The media was removed and fresh compound +/− the toxic stimuli are added. The cells were then incubated for 24 hrs at 37° C. Following the incubation the media was collected and used for analysis in the CytTox 96 Nonradioactive Cytotoxicity Assay. Briefly, the LDH release from the dead cells was quantified in a 30 min enzymatic reaction that resulted in the conversion of a chondrocytes, and is known to be stimulated potently by IL-1, which, like NO and peroxynitrite is held to be a major pathogenic factor in osteoarthritis. Thus, GAG release assays were carried out on Compound 9DBC, in which, to optimize the screening assay, a one hour digestion of the cartilage "nodules" formed in the polyheme system was carried out using 300 ug/ml of papain in 20 mM sodium phosphate, 1 mM EDTA, and 2mM DTT (pH 6.8). The digestion of the interfering proteins accomplished in this manner allowed the GAG release to be more readily detectable, and the GAG release was quantified by the standard dimethylene blue (DMB) dye binding colorimetric assay. In brief, the cell extract digested from above was combined with 46 uM DMB, 40 mM glycine and 40 mM NaCl (pH 3.0) and immediately read at 525 nm and compared again a standard curve of 1–50 ug/ml chondroitin sulfate.

Bovine Cartilage Organ Culture Methods

Mature bovine knees were obtained and cartilage from the femoral condyles and patellar groove was removed in full thickness slices (1–3mm). Circular cores (6–7 mm in diameter) were punched out of the tissue. The cores were washed twice with media (1% FCS, 1% P/S, 1% glutamine containing DMEM high glucose) and then placed in 96 wells plates. The slices were incubated in media (as above) at 37° C. for 48 hrs to allow for recovery from the isolation process. After the recovery period, the media was removed and fresh media with Compound 9DBC was added to the slices for a pretreatment period of 6 hrs. Then the media was removed and fresh compound plus/minus IL-1 was added and incubated at 37° C. for 24 hrs. The conditioned media was collected and the GAG and NO release were analyzed. Finally the slices were weighed to correct for slight variations in size or thickness.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A compound having the structure:

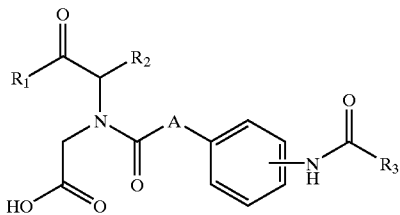

or a stereoisomer, prodrug or pharmaceutically acceptable salt thereof,
wherein:
- A is a direct bond, alkyldiyl, substituted alkyldiyl, —O-(alkyldiyl)-, —O-(substituted alkyldiyl)-, -(alkyldiyl)—O—, -(substituted alkyldiyl)—O—, —N(R')-(alkyldiyl)-, —N(R')-(substituted alkyldiyl)-, -(alkyldiyl)-N(R')—, -(substituted alkyldiyl)-N(R')—, heterocyclediyl, substituted heterocyclediyl, heterocyclealkyldiyl or substituted heterocyclealkyldiyl, wherein R' is hydrogen or alkyl;
- $R_1$ is hydroxy, alkoxy, aryloxy, arylalkyloxy, amino, or mono- or di-alkylamino;
- $R_2$ is hydrogen, alkyl, substituted alky, aryl, substituted aryl, arylalkyl, substituted arylalkyl, heterocycle, substituted heterocycle, heterocyclealkyl or substituted heterocyclealkyl; and
- $R_3$ is alkyl, substituted alky, aryl, substituted aryl, arylalkyl, substituted arylalkyl, heterocycle, substituted heterocycle, heterocyclealkyl or substituted heterocyclealkyl.

2. The compound of claim 1 wherein $R_1$ is hydroxy.
3. The compound of claim 1 wherein $R_1$ is alkyoxy.
4. The compound of claim 3 wherein $R_1$ is methoxy.
5. The compound of claim 1 wherein $R_1$ is amino.
6. The compound of claim 1 wherein $R_1$ is aryloxy or arylalkyloxy.
7. The compound of claim 1 wherein $R_2$ is hydrogen.
8. The compound of claim 1 where $R_2$ is alkyl.
9. The compound of claim 1 wherein $R_3$ is alkyl.
10. The compound of claim 1 wherein $R_3$ is substituted alkyl.
11. The compound of claim 1 wherein A is a direct bond.
12. The compound of claim 1 wherein A is alkyldiyl.
13. The compound of claim 1 wherein A is —O-(alkyldiyl)- or -(alkyldiyl)—O—.
14. The compound of claim 1 wherein A is —N(R') alkyldiyl- or -(alkyldiyl)-N(R')—.
15. The compound of claim 1 wherein A is heterocyclediyl.
16. The compound of claim 1 wherein A is heterocyclealkyldiyl.
17. A pharmaceutical composition comprising a compound of claim 1 in combination with a pharmaceutically acceptable carrier.
18. A method for neuroprotection, comprising administering to an animal in need thereof, a neuroprotective effective amount of the composition of claim 17.

* * * * *